United States Patent
Gonçalves Leite De Assunçao et al.

(10) Patent No.: US 10,870,862 B2
(45) Date of Patent: *Dec. 22, 2020

(54) REGULATION OF ZINC DEFICIENCY AND TOLERANCE IN PLANTS

(71) Applicant: WAGENINGEN UNIVERSITEIT, Wageningen (NL)

(72) Inventors: Ana Gonçalves Leite De Assunçao, Maia (PT); Martinus Gerardus Maria Aarts, Wageningen (NL)

(73) Assignee: WAGENINGEN UNIVERSITEIT, Wageningen (NL)

( * ) Notice: Subject to any disclaimer, the term of this patent is extended or adjusted under 35 U.S.C. 154(b) by 65 days.

This patent is subject to a terminal disclaimer.

(21) Appl. No.: 16/165,947

(22) Filed: Oct. 19, 2018

(65) Prior Publication Data

US 2019/0106704 A1    Apr. 11, 2019

Related U.S. Application Data

(62) Division of application No. 13/383,808, filed as application No. PCT/NL2010/050461 on Jul. 16, 2010, now Pat. No. 10,106,810.

(30) Foreign Application Priority Data

Jul. 16, 2009  (EP) ................................. 09165714

(51) Int. Cl.
  *C12N 15/82*  (2006.01)
  *C07K 14/415* (2006.01)

(52) U.S. Cl.
  CPC ........ *C12N 15/8271* (2013.01); *C07K 14/415* (2013.01); *C12N 15/8237* (2013.01); *C12N 15/8259* (2013.01)

(58) Field of Classification Search
  None
  See application file for complete search history.

(56) References Cited

U.S. PATENT DOCUMENTS

| | | | |
|---|---|---|---|
| 10,106,810 B2 * | 10/2018 | Goncalves Leite De Assuncao | ............ C07K 14/415 |
| 2007/0022495 A1 * | 1/2007 | Reuber | .............. C12N 15/8261 800/279 |
| 2008/0148432 A1 | 6/2008 | Abad | |
| 2009/0044288 A1 | 2/2009 | Abad | |

OTHER PUBLICATIONS bZIP transcription factor family protein, GenBank Accession No. NP_567974, published Jun. 19, 2009, p. 1.

(Continued)

*Primary Examiner* — Ashley K Buran
(74) *Attorney, Agent, or Firm* — Morrison & Foerster LLP

(57) ABSTRACT

The invention relates to a method to change the capacity of a plant for adaptation to changes in the zinc concentration in the environment, especially the soil, comprising providing said plant with a nucleotide according to SEQ ID NO:1 or SEQ ID NO: 2 or an ortholog thereof. Such a method is especially useful to decrease Zn deficiency or to (hyper) accumulate Zn in plants for bioremediation or for biofortification. Transgenic plants for these proteins are also disclosed.

7 Claims, 10 Drawing Sheets
(8 of 10 Drawing Sheet(s) Filed in Color)

Specification includes a Sequence Listing.

(56) References Cited

OTHER PUBLICATIONS

Cakmak, "Enrichment of cereal grains with zinc: Agronomic or genetic biofortification?" Plant Soil (2008) 302:1-17.
Dalcorso et al., "How Plants Cope with Cadmium: Staking All on Metabolism and Gene Expression," Journal of Integrative Plant Biology (2008) 50(10):1268-1280.
Day et al., "Transgene integration into the same chromosome location can produce alleles that express at a predictable level, or alleles that are differentially silenced," Genes Development (2000) 14:2869-2880.
DNA binding/transcription factor, GenBank Accession No. NP_179268, published Jun. 19, 2009, p. 1.
Ghandilyan et al., "Progres in the genetic understanding of plant iron and zinc nutrition," Physiologia Plantarum (2006) 126:407-417.
International Search Report for PCT/NL2010/050461, dated Oct. 5, 2010, 3 pages.
Jakoby et al., "bZIP transcription factors in *Arabidopsis*," Trends in Plant Science (2002) 7(3):106-111.
Lin et al., "Sequence and analysis of chromosome 2 of the plant *Arabidopsis thaliana*," Nature (1999) 402:761-768.
Morel et al., "AtHMA3, a P1B-ATPase allowing Cd/Zn/Co/Pb vacuolar storage in *Arabidopsis*," Plant Physiology (2009) 149:894-904.
Peach et al., "Transgene expression variability (position effect) of CAT and GUS reporter genes driven by linked divergent T-DNA promoter," Plant Molecular Biology (1991) 17:49-60.
Van Der Zaal et al., "Overexpression of a Novel *Arabidopsis* Gene Related to Putative Zinc-Transporter Genes from Animals Can Lead to Enhanced Zinc Resistance and Accumulation," Plant Physiology (1999) 119:1047-1055.
Verret et al., "Overexpression of AtHMA4 enhances root-to-shoot translocation of zinc and cadmium and plant metal tolerance," FEBS Letters (2004) 576:306-312.

\* cited by examiner

FIG. 1

```
bZIP23      ----------MDDGELEFSNSNMGG-------ELPSCSMDSFFDELLRDS-HACTHTHT  41
bZIP19      ----------MEDGELDFSNQEVFSSSEMGELPPSNCSMDSFFDGLLMDTNAACTHTHT  49
bZIP24      MFCCCKDCRGNQRVSNFDSLTGVFFGDLEFGPQNQRYIKMNEEEDKDQDRVTRGCSHTHS  60
              ::         .::: .  .  . :    .*: . *          .*:***:

bZIP23      CNPPGPE-NTHTHTCLHVHTKILP----DKVSTDDTSESSGK--KRPIGNREAVRHIRE  93
bZIP19      CNPTGPE-NTHTHTCFHVHTKILPDESDEKVSTDDTAESCGKKGEYRPLGNRAVHRKRE 108
bZIP24      CNPPGPEDASHSHICFHAHTHLIIS---QDQQENDHSDSSNK--KRLCGNREAVRHINE 114
            *.*  :*:***:*.**:::      :.. :* ::*..*      ******* bZIP23      KKRKTAASLEDEVMRLRAVNNQLKRLQGQAALEAEVTRLKCLLVDIRGRIDGEIGAFPY 153
bZIP19      KKAAKAASLEDEVARLRAVNQQLVKRLQNQATLEAEVSRLKCLLVDLRGRIDGEIGSFPY 168
bZIP24      KKRKTAVLEDEVMRLGSLNEQFLRKLQSQEMVETELIRLRALLVEMQGKIEVELCSFSF 174
            ****::* ***** **::::*:*:::::**.*  :*:*: **:.***::*:*: *: :*.:

bZIP23      QKPAVTNVP-YSYMMHPCNMQCDVDNLYCLQNG--NNGEGASMNEQGLNGCEFDQLECLA 210
bZIP19      QKPMAANIPSFSHMMNPCNVQCDDEVYCPQNVFGVNSQEGASINDQGLSGCDFDQLQCMA 228
bZIP24      QK--QCNGSGFVFKEDGCNLATSN---------------------MMCEAARVECEE 208
            **   *  . :  . **:  .                            *:  :::* bZIP23      NQNLAGKEIPVCSNGIGTFTVNGSGVNKRKGEPRAAKAV 249
bZIP19      NQNLNGNGNGSFSN------VNTSVSNKRKGGHRASRAV 261
bZIP24      GQTLHDPIQSFVPQ---------------PPPFSR-- 228
            .*.*  .    .:                   ::
```

REGULATION OF ZINC DEFICIENCY AND TOLERANCE IN PLANTS

CROSS-REFERENCE TO RELATED APPLICATIONS

This Application is a divisional of application Ser. No. 13/383,808 (allowed) having an international filing date of 16 Jul. 2010, which is the national phase of PCT application PCT/NL2010/050461 having an international filing date of 16 Jul. 2010, which claims benefit of European patent application No. 09165714.8 filed 16 Jul. 2009. The contents of the above patent applications are incorporated by reference herein in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP § 1730 II.B.2(a)(C), is incorporated herein by reference in its entirety for all purposes. The sequence listing is identified on the electronically filed text file as follows:

| File Name | Date of Creation | Size (bytes) |
|---|---|---|
| 313632012910SeqList | Oct. 18, 2018 | 28,751 |

FIELD OF THE INVENTION

The invention relates to plant biotechnology, more specifically to modulate the sensitivity to metals in plants, more specifically to Zn. Particularly, the invention relates to adaptation of the plant to changes in the availability of Zn in the environment.

BACKGROUND OF THE INVENTION

Zinc is an essential micronutrient for all living organisms including plants. Zinc is typically the second most abundant transition metal in organisms after iron (Fe), and the only metal represented in all six enzyme classes (oxidoreductases, transferases, hydrolases, lyases, isomerases and ligases). Zinc binding sites also occur in a wide range of other proteins, membrane lipids and DNA/RNA molecules. The largest class of Zn-binding proteins in organisms is the zinc finger domain containing proteins that function as transcription regulator.

Zn is present in the soil in primarily three fractions: (i) water-soluble Zn (including $Zn^{2+}$ and soluble organic fractions), (ii) adsorbed and exchangeable Zn in the colloidal fraction (associated with clay particles) and (iii) insoluble Zn complexes and minerals. Zinc is acquired from the soil solution primarily as $Zn^{2+}$, but also potentially complexed with organic ligands, by roots which feed their shoots via the xylem.

When facing a shortage in zinc supply, plants adapt by enhancing the zinc uptake capacity. Plants are thought to control Zn homeostasis using a tightly regulated network of zinc status sensors and signal transducers controlling the coordinated expression of Zn transporters involved in Zn acquisition from the soil, mobilization between organs and tissues and sequestration within cellular components (Clemens, S., 2001, Planta 212:475-486).

In recent years numerous studies have been performed to unravel the biochemical pathways of Zn uptake and transport. In these studies, however, it is not yet found which proteins are responsible for Zn uptake from the soil (Palmer, C. M. and Guerinot, M. L., 2009, Nature Chem. Biol. 5:333-340). While candidate genes for the required Zn transporters have been identified, the so-called ZIP transporters ZIP1, ZIP2, ZIP3 and ZIP4 (Grotz, N. et al., 1998, Proc. Natl. Acad. Sci USA 95:7220-7224), more proteins seem to be necessary to explain the phenomenon of Zn-hyperaccumulation, such as the heavy metal transporters HMA2, 3 and 4 (Hanikenne et al, 2008, Nature 453:391-395). Also nicotianamine, made by nicotianamine synthase (NAS), seems to play a role in vascular transport of zinc, and the citrate transporter FRD3 (Durrett, T. P. et al., 2007, Plant Physiol. 144:197-205). For transport between tissues and organs several proteins seem to be involved. Members of the YSL group, a subfamily of the oligopeptide transporter (OPT) family of transporters, are proteins that have been mentioned. For intracellular transport of Zn, NRAMP ZIP and ZIF proteins seem to be involved. Transport of Zn into the vacuole is performed by MTPs (metal tolerance proteins, also referred to as cation diffuser facilitator-CDF-proteins).

(Lack of) adaptation of plants to a changing concentration of Zn in the environment works both ways: zinc deficiency and zinc toxicity. After Fe deficiency, Zn deficiency is the most commonly occurring micronutrient deficiency in agriculture, mainly affecting parts of Asia (Turkey and Near-East Asia, Central Asia, South and Central China), Sahel and sub-Saharan Africa and Australia. Since plants are often the major dietary source of micronutrients for human consumption, many people worldwide suffer from Fe and Zn deficiencies as plants, especially cereals, are notoriously poor in their content of bioavailable Fe and Zn.

Some soils are not deficient in minerals, but have become contaminated with large amounts of heavy metals, such as Zn or Cd. Zn toxicity in crops is far less widespread than Zn deficiency. However, toxicity symptoms usually become visible at Zn concentrations of more than 300 mg Zn $kg^{-1}$ in the leaves. Some plants are known to be able to grow on soil that has a high concentration of Zn, such as Silene vulgaris, Thlaspi caerulescens, Arabidopsis halleri and Viola calaminaria (see also Table 3 in Broadley, M. R. et al., 2007, New Phytologist 173:677-702). It has been suggested to use these Zn hyperaccumulators as sanitation plants to extract zinc from the soil, whereby the metal is concentrated in the biomass, that can be harvested, incinerated and properly disposed of. Such a method, known as phytoremediation, is currently not attractive as the known metal hyperaccumulator plants are relatively small, thus producing not sufficient biomass to yield a high metal extraction capacity.

Thus, there is still need to be able to control the adaptation of plants to changes in zinc concentration in the environment.

SUMMARY OF THE INVENTION

The invention now relates to a method to change the capacity of a plant for adaptation to changes in the zinc concentration in the environment, especially the soil, comprising providing said plant with a nucleotide coding for a bZIP19 and/or bZIP23 protein or a functional equivalent thereof. Preferably in such a method the tolerance to Zn deficiency is increased. In another embodiment in such a method said plant is capable of hyperaccumulating zinc. In a further embodiment said plant is capable of enhancing concentrations of zinc in edible parts.

In the above mentioned methods, the plant is preferably provided with a nucleotide coding for a bZIP19 protein and a nucleotide coding for a bZIP23 protein. More preferably, said plant is additionally provided with one or more polynucleotides coding for a protein selected from the group consisting of heavy metal transporters, preferably HMA2, HMA3 or HMA4, YSL proteins, preferably YSL, preferably YSL1 or YSL3, ZIP or IRT proteins, ZIF proteins, NAS proteins, MRP proteins, FRD3 and MTPs.

The invention further relates to a plant transformed with a polynucleotide coding for a bZIP19 and/or a bZIP23 protein.

The invention further comprises a method according as described above or a plant as described above, wherein the polynucleotide is derived from *Arabidopsis*, more preferably *A. thaliana*.

The invention further relates to a plant made by a method according to the invention, preferably wherein said plant overexpresses a bZIP19 and/or a bZIP23 protein. Preferably said plant is tolerant to Zn deficiency. Alternatively, said plant is a Zn hyperaccumulator and/or has an elevated amount of bioavailable Zn in its edible parts.

Also part of the invention is a method for phytoremediation, comprising growing a plant according to the invention on soil that is polluted with Zn, harvesting said plant and disposing of the biomass. Further part of the invention is a method for biofortification, comprising growing a plant according to to the invention on soil that is polluted with Zn, harvesting said plant and disposing of the biomass.

Also part of the invention is the use of the (nucleotides encoding) the bZIP19 and/or bZIP protein in the methods of the invention and/or for producing the plants of the invention.

BRIEF DESCRIPTION OF THE DRAWINGS

The patent application file contains at least one drawing executed in color. Copies of this patent or patent application publication with color drawing(s) will be provided by the Office upon request and payment of the necessary fee.

FIG. 1: Amino acid sequences of *Arabidopsis thaliana* proteins bZIP19 (SEQ ID NO:2), bZIP23 (SEQ ID NO:1) and bZIP24 (SEQ ID NO:3). Amino acids highlighted in green correspond to the bZIP domain. Amino acids highlighted in grey correspond to two conserved motifs rich in histidine residues. An asterisk or dot below the aligned sequences indicates identical, respectively, similar amino acids.

FIG. 2A Schematic diagram of the baits (A-G) used to construct the reporter vectors in the yeast-one-hybrid assay. The grey box represents the 10-bp palindromic motif. FIG. 2B Relative transcript levels (RTL) of bZIP19, bZIP23 and bZIP24 in 3-week-old *Arabidopsis* seedlings grown in MS medium, without (Zn−), with 30 μM (Zn+) or with 300 μM ZnSO$_4$ (Zn++). Error bars indicate SE.

FIG. 3A Relative transcript levels (RTL) of ZIP4 in 3-week-old *Arabidopsis* seedlings grown in MS medium, with 30 μM ZnSO$_4$ (Zn+) or without (Zn−). Error bars indicate SE. FIG. 3B Growth of zrt1zrt2 *S. cerevisiae* cells carrying either the empty vector (zrt1zrt2 Ø) or expressing ZIP4 (zrt1zrt2 ZIP4) was assayed by spotting serial dilutions of cells (OD$_{600}$ is shown on the left) on SD-URA selective medium with 0.4 or 0.8 mM ZnCl$_2$. FIG. 3C OD measurements at the indicated time-intervals of zrt1zrt2 Ø and zrt1zrt2 ZIP4 on SD-URA selective liquid medium with 0.4 mM ZnCl$_2$. Error bars indicate SE.

FIG. 4A Effect of zinc deficiency on 3-week-old seedlings of *Arabidopsis* (WT), bZIP19 T-DNA insertion mutants, m19, bZIP23 T-DNA insertion mutants, m23, and double T-DNA insertion mutants, m19m23, grown in MS medium without (Zn−) and with 30 μM ZnSO$_4$ (Zn+). FIG. 4B Effect of zinc supply on 4-week-old plants of *Arabidopsis* (WT), m19, m23 and m19m23, grown in hydroponics at 0.05 μM (Zn−), 2 μM (Zn+) and 25 μM ZnSO$_4$ (Zn++). FIG. 4C Zinc concentration, in mg kg$^{-1}$ dry weight, and dry weight (DW), in g, of roots (white bars) and shoots (grey bars) of 4-week-old WT, m19, m23 and m19m23 plants, grown in hydroponics at 0.05 μM ZnSO$_4$ (Zn−). *P<0.05, P<0.01, *P<0.001; representing significant differences of the mean in comparison with the WT mean. Error bars indicate SE.

FIG. 5A Schematic drawing of the bZIP19 mutant allele (m19) and the bZIP23 mutant allele (m23). Triangles indicate T-DNA insertions. White boxes indicate exons, grey boxes indicate introns, lines indicate 5' and 3' untranslated sequences. FIG. 5B Relative transcript levels (RTL) of bZIP19 (white bars) and bZIP23 (grey bars) in 3-week-old seedlings of *Arabidopsis* wild type plants (WT), homozygous bZIP19 T-DNA insertion mutants (m19), homozygous bZIP23 T-DNA insertion mutants (m23), and T-DNA insertion double mutants (m19m23) grown in MS medium. Error bars indicate SE.

FIG. 8A *Arabidopsis* wild-type plants (WT), double T-DNA insertion mutants (m19m23) and double mutants constitutively expressing either bZIP19 (m19m23OX19) or bZIP23 (m19m23OX23), grown for 4 weeks in MS medium without (Zn−) and with 30 μM ZnSO$_4$ (Zn+). FIG. 8B Relative transcript levels (RTL) of ZIP4, ZIP1, ZIP3, ZIP5, ZIP9, ZIP12, IRT3 and ZIP2 in 3-week-old wild-type seedlings of *Arabidopsis* (WT) (white bars) and m19m23 double mutants (grey bars) grown in MS medium with 30 μM ZnSO$_4$ (Zn+) or without (Zn−). Error bars indicate SE.

DEFINITIONS

Figure 2A:
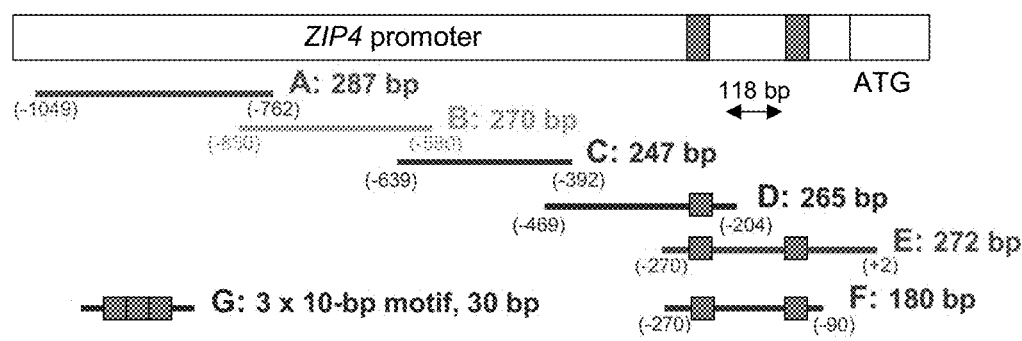
FIG. 2A-2B: Yeast-one-hybrid baits and F group bZIP gene expression.

The term "gene" is used broadly to refer to any segment of nucleic acid associated with a biological function. Thus, genes include coding sequences and/or the regulatory sequences required for their expression. For example, gene refers to a nucleic acid fragment that expresses mRNA or functional RNA, or encodes a specific protein, and which includes regulatory sequences. Genes also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

The term "native" or "wild type" gene refers to a gene that is present in the genome of an untransformed cell, i. e., a cell not having a known mutation. The term "native" or "wild type" is intended to encompass allelic variants of the gene.

A "marker gene" encodes a selectable or screenable trait. The term "selectable marker" refers to a polynucleotide sequence encoding a metabolic trait which allows for the separation of transgenic and non-transgenic organisms and mostly refers to the provision of antibiotic resistance. A selectable marker is for example the aph (npt) encoded kanamycin resistance marker, or the hpt gene, the gene coding for hygromycin resistance. Other selection markers are for instance reporter genes such as chloramphenicol acetyl transferase, β-galactosidase, luciferase and green fluorescence protein. Identification methods for the products of reporter genes include, but are not limited to, enzymatic assays and fluorimetric assays. Reporter genes and assays to detect their products are well known in the art and are described, for example in Current Protocols in Molecular Biology, eds. Ausubel et al., Greene Publishing and Wiley-Interscience: New York (1987) and periodic updates.

The term "chimeric gene" refers to any gene that contains 1) nucleotide sequences, including regulatory and coding sequences, that are not found together in nature, or 2) nucleotide sequences encoding parts of proteins not naturally adjoined, or 3) parts of promoters that are not naturally adjoined. Accordingly, a chimeric gene may comprise regulatory sequences and coding sequences that are derived from different sources, or comprise regulatory sequences and coding sequences derived from the same source, but arranged in a manner different from that found in nature.

A "transgene" refers to a gene that has been introduced into the genome by transformation and that preferably is stably maintained. Transgenes may include, for example, genes that are either heterologous or homologous to the genes of a particular plant to be transformed. Additionally, transgenes may comprise native genes inserted into a non-native organism or chimeric genes. The term "endogenous gene" refers to a native gene in its natural location in the genome of an organism. A "foreign" gene refers to a gene not normally found in the host organism but that is introduced by gene transfer.

An "oligonucleotide", e. g., for use in probing or amplification reactions, may be about 30 or fewer nucleotides in length (e. g., 9, 12, 15, 18, 20, 21 or 24, or any number between 9 and 30). Generally specific primers are upwards of 14 nucleotides in length. For optimum specificity and cost effectiveness, primers of 16 to 24 nucleotides in length may be preferred. Those skilled in the art are well versed in the design of primers for use in processes such as PCR. If required, probing can be done with entire restriction fragments of the gene disclosed herein which may be 100's or even 1000's of nucleotides in length.

The terms "protein", "peptide" and "polypeptide" are used interchangeably herein.

"Coding sequence" refers to a nucleotide (DNA or RNA) sequence that codes for a specific amino acid sequence and excludes the non-coding sequences. It may constitute an "uninterrupted coding sequence", i. e., lacking an intron, such as in a cDNA or it may include one or more introns bound by appropriate splice junctions. An "intron" is a sequence of RNA which is contained in the primary transcript but which is removed through cleavage and re-ligation of the RNA within the cell to create the mature mRNA that can be translated into a protein. Also the DNA coding for said sequence of RNA is designated as "intron". "Exons" are the coding parts of the DNA or RNA sequence, which are separated from each other by introns.

"Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences include enhancers, promoters, translation leader sequences, introns, and polyadenylation signal sequences. They include natural and synthetic sequences as well as sequences which may be a combination of synthetic and natural sequences. As is noted above, the term "suitable regulatory sequences" is not limited to promoters.

"Promoter" refers to a nucleotide sequence, usually upstream (5') to its coding sequence, which controls the expression of the coding sequence by providing the recognition for RNA polymerase and other factors required for proper transcription. "Promoter" includes a minimal promoter that is a short DNA sequence comprised of a TATA box and other sequences that serve to specify the site of transcription initiation, to which regulatory elements are added for control of expression. "Promoter" also refers to a nucleotide sequence that includes a minimal promoter plus regulatory elements that is capable of controlling the expression of a coding sequence or functional RNA. This type of promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue specificity of a promoter. It is capable of operating in both orientations (normal or flipped), and is capable of functioning even when moved either upstream or downstream from the promoter. Both enhancers and other upstream promoter elements bind sequence-specific DNA-binding proteins that mediate their effects. Promoters may be derived in their entirety from a native gene, or be composed of different elements derived from different promoters found in nature, or even be comprised of synthetic DNA segments. A promoter may also contain DNA sequences that are involved in the binding of protein factors which control the effectiveness of transcription initiation in response to physiological or developmental conditions.

The "initiation site" is the position surrounding the first nucleotide that is part of the transcribed sequence, which is also defined as position+1. With respect to this site all other sequences of the gene and its controlling regions are numbered. Downstream sequences (i. e., further protein encoding sequences in the 3' direction) are denominated positive, while upstream sequences (mostly of the controlling regions in the 5'direction) are denominated negative.

"Constitutive expression" refers to expression using a constitutive promoter.

"Conditional" and "regulated expression" refer to expression controlled by a regulated promoter.

"Constitutive promoter" refers to a promoter that is able to express the open reading frame (ORF) that it controls in all or nearly all of the plant tissues during all or nearly all developmental stages of the plant.

The terms "open reading frame" and "ORF" refer to the amino acid sequence encoded between translation initiation and termination codons of a coding sequence. The terms "initiation codon" and "termination codon" refer to a unit of three adjacent nucleotides ('codon') in a coding sequence that specifies initiation and chain termination, respectively, of protein synthesis (mRNA translation).

"Regulated promoter" refers to promoters that direct gene expression not constitutively, but in a temporally- and/or spatially-regulated manner, and includes both tissue-specific and inducible promoters. It includes natural and synthetic sequences as well as sequences which may be a combination of synthetic and natural sequences. Different promoters may direct the expression of a gene in different tissues or cell types, or at different stages of development, or in response to different environmental conditions. New promoters of various types useful in plant cells are constantly being discovered, numerous examples may be found in the compilation by Okamuro, J. K. and Goldberg, R. B. (1989) Chapter 1, "Regulation of Plant Gene Expression: General Principles" in Stumpf, P. K. and Conn, E. E. Eds., *The Biochemistry of Plants: A comprehensive treatise*. Academic Press, NY USA).

"Tissue-specific promoter" refers to regulated promoters that are not expressed in all plant cells but only in one or more cell types in specific organs (such as roots, stems, leaves or seeds), specific tissues (such as embryo or cotyledon), or specific cell types (such as leaf parenchyma or seed storage cells).

"Operably-linked" refers to the association of nucleic acid sequences on a single nucleic acid fragment so that the function of one is affected by the other. For example, a regulatory DNA sequence is said to be "operably linked to" or "associated with" a DNA sequence that codes for an RNA or a polypeptide if the two sequences are situated such that the regulatory DNA sequence affects expression of the coding DNA sequence (i. e., that the coding sequence or functional RNA is under the transcriptional control of the promoter). Coding sequences can be operably-linked to regulatory sequences in sense or antisense orientation.

"Expression" refers to the transcription and/or translation of an endogenous gene, ORF or portion thereof, or a transgene in plants. Expression refers to the transcription and stable accumulation of sense (mRNA) or functional RNA. Expression may also refer to the production of protein.

"Specific expression" is the expression of gene products which is limited to one or a few plant tissues (spatial limitation) and/or to one or a few plant developmental stages (temporal limitation). It is acknowledged that hardly a true specificity exists: promoters seem to preferably switch on in some tissues, while in other tissues there can be no or only little activity. This phenomenon is known as leaky expression. However, with tissue-specific expression in this invention is meant preferable expression in one or a few plant tissues.

The terms "heterologous DNA sequence", "exogenous DNA segment" or "heterologous nucleic acid", as used herein, each refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides. A "homologous" DNA sequence is a DNA sequence that is naturally associated with a host cell into which it is introduced.

"Homologous to" in the context of nucleotide or amino acid sequence identity refers to the similarity between the nucleotide sequence of two nucleic acid molecules or between the amino acid sequences of two protein molecules. Estimates of such homology are provided by either DNA-DNA or DNA-RNA hybridization under conditions of stringency as is well understood by those skilled in the art (as described in Haines and Higgins (eds.), Nucleic Acid Hybridization, IRL Press, Oxford, U. K.), or by the comparison of sequence similarity between two nucleic acids or proteins. Two nucleotide or amino acid sequences are homologous when their sequences have a sequence similarity of more than 60%, preferably more than 70%, 80%, 85%, 90%, 95%, or even 98%.

The term "substantially similar" refers to nucleotide and amino acid sequences that represent functional and/or structural equivalents of sequences disclosed herein. For example, altered nucleotide sequences which simply reflect the degeneracy of the genetic code but nonetheless encode amino acid sequences that are identical to a particular amino acid sequence are substantially similar to the particular sequences. In addition, amino acid sequences that are substantially similar to a particular sequence are those wherein overall amino acid identity is at least 65% or greater to the instant sequences. Modifications that result in equivalent nucleotide or amino acid sequences are well within the routine skill in the art. Moreover, the skilled artisan recognizes that equivalent nucleotide sequences encompassed by this invention can also be defined by their ability to hybridize, under low, moderate and/or stringent conditions (e. g., 0.1×SSC, 0.1% SDS, 65° C.), with the nucleotide sequences that are within the literal scope of the instant claims.

The term "transformation" refers to the transfer of a nucleic acid fragment into the genome of a host cell, resulting in genetically stable inheritance. Host cells containing the transformed nucleic acid fragments are referred to as "transgenic" cells, and organisms comprising transgenic cells are referred to as "transgenic organisms". Examples of methods of transformation of plants and plant cells include *Agrobacterium*-mediated transformation (De Blaere et al., 1987) particle bombardment technology (Klein et al. 1987; U.S. Pat. No. 4,945,050), microinjection, CaPO$_4$ precipitation, lipofection (liposome fusion), use of a gene gun and DNA vector transporter (Wu et al., 1992). Whole plants may be regenerated from transgenic cells by methods well known to the skilled artisan (see, for example, Fromm et al., 1990).

"Transformed", "transgenic" and "recombinant" refer to a host organism such as a bacterium or a plant into which a heterologous nucleic acid molecule has been introduced. The heterologous nucleic acid molecule can be stably integrated into the genome generally known in the art and are disclosed in Sambrook et al., 1989. See also Innis et al., 1995 and Gelfand, 1995; and Innis and Gelfand, 1999. For example, "transformed", "transformant", and "transgenic" plants or calli have been through the transformation process and contain a foreign gene integrated into their chromosome. The term "untransformed" refers to normal plants that have not been through the transformation process.

"Transiently transformed" refers to cells in which transgenes and foreign DNA have been introduced (for example, by such methods as *Agrobacterium*-mediated transformation or biolistic bombardment), but not selected for stable maintenance.

"Stably transformed" refers to cells that have been selected and regenerated on a selection media following transformation.

"Genetically stable" and "heritable" refer to chromosomally-integrated genetic elements that are stably maintained in the plant and stably inherited by progeny through successive generations.

"Chromosomally-integrated" refers to the integration of a foreign gene or DNA construct into the host DNA by covalent bonds. Where genes are not "chromosomally integrated" they may be "transiently expressed". Transient expression of a gene refers to the expression of a gene that is not integrated into the host chromosome but functions independently, either as part of an autonomously replicating plasmid or expression cassette, for example, or as part of another biological system such as a virus.

"Primary transformant" refers to transgenic plants that are of the same genetic generation as the tissue which was initially transformed (i. e., not having gone through meiosis and fertilization since transformation).

"Secondary transformants" and the "T1, T2, T3, etc. generations" refer to transgenic plants derived from primary transformants through one or more meiotic and fertilization cycles. They may be derived by self-fertilization of primary or secondary transformants or crosses of primary or secondary transformants with other transformed or untransformed plants. Secondary transformants are an aspect of the present invention.

"Genome" refers to the complete genetic material of an organism.

The term "nucleic acid" or "polynucleotide" refers to deoxyribonucleotides or ribonucleotides and polymers thereof in either single- or double-stranded form, composed of monomers (nucleotides) containing a sugar, phosphate and a base which is either a purine or pyrimidine. Unless specifically limited, the term encompasses nucleic acids containing known analogs of natural nucleotides which have similar binding properties as the reference nucleic acid and are metabolized in a manner similar to naturally occurring nucleotides. Unless otherwise indicated, a particular nucleic acid sequence also implicitly encompasses conservatively modified variants thereof (e. g., degenerate codon substitutions) and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., 1991; Ohtsuka et al., 1985; Rossolini et al. 1994). A "nucleic acid fragment" is a fraction of a given nucleic acid molecule. In higher plants, deoxyribonucleic acid (DNA) is the genetic material while ribonucleic acid (RNA) is involved in the transfer of information contained within DNA into proteins. The term "nucleotide sequence" refers to a polymer of DNA or RNA which can be single- or double-stranded, optionally containing synthetic, non-natural or altered nucleotide bases capable of incorporation into DNA or RNA polymers. The terms "nucleic acid" or "nucleic acid sequence" may also be used interchangeably with gene, cDNA, DNA and RNA encoded by a gene.

The nucleotide sequences used in aspects of the invention include both the naturally occurring sequences as well as mutant (variant) forms. Such variants will continue to possess the desired activity, i. e., either promoter activity or the activity of the product encoded by the open reading frame of the non-variant nucleotide sequence.

Thus, by "variant" is intended a substantially similar sequence. For nucleotide sequences comprising an open reading frame, variants include those sequences that, because of the degeneracy of the genetic code, encode the identical amino acid sequence of the native protein. Naturally occurring allelic variants such as these can be identified with the use of well-known molecular biology techniques, as, for example, with polymerase chain reaction (PCR) and hybridization techniques. Variant nucleotide sequences also include synthetically derived nucleotide sequences, such as those generated, for example, by using site-directed mutagenesis and for open reading frames, encode the native protein, as well as those that encode a polypeptide having amino acid substitutions relative to the native protein. Generally, nucleotide sequence variants of the invention will have at least 40, 50, 60, to 70%, e. g., preferably 71%, 72%, 73%, 74%, 75%, 76%, 77%, 78%, to 79%, generally at least 80%, e. g., 81%-84%, at least 85%, e. g., 86%, 87%, 88%, 89%, 90%, 91%, 92%, 93%, 94%, 95%, 96%, 97%, to 98% and 99% nucleotide sequence identity to the native (wild type or endogenous) nucleotide sequence.

The term "nucleotide sequence identity" or "nucleotide sequence homology" as used herein denotes the level of similarity, respectively the level of homology, between two polynucleotides. Polynucleotides have "identical" sequences if the sequence of nucleotides in the two sequences is the same. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence identity" or "percentage of sequence homology" for polynucleotides, such as 50, 60, 70, 80, 90, 95, 98, 99 or 100 percent sequence identity or homology may be determined by comparing two optimally aligned sequences over a comparison window, wherein the portion of the polynucleotide sequence in the comparison window may include additions or deletions (i.e. gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST) (Altschul et al., 1990; Altschul et al., 1997) and ClustalW programs, both available on the internet. Other suitable programs include, but are not limited to, GAP, BestFit, PlotSimilarity, and FASTA in the Wisconsin Genetics Software Package (Genetics Computer Group (GCG), Madison, Wis., USA) (Devereux et al., 1984).

The nucleic acid sequences of the invention can be "optimized" for enhanced expression in plants of interest. See, for example, EP 0359472 or WO 91/16432. In this manner, the open reading frames in genes or gene fragments can be synthesized utilizing plant-preferred codons. Thus, the nucleotide sequences can be optimized for expression in any plant.

By "variant" polypeptide is intended a polypeptide derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art. Also included in the definition of variant polypeptide are "orthologous" polypeptides (orthologs), which are peptides encoded by genes in different species that evolved from a common ancestral gene by speciation. Normally, orthologs retain the same function in the course of evolution Thus, the polypeptides may be altered in various ways including amino acid substitutions, deletions, truncations, and insertions. Methods for such manipulations are generally known in the art. Conservative substitutions, such as exchanging one amino acid with another having similar properties, are preferred. Individual substitutions deletions or additions that alter, add or delete a single amino acid or a small percentage of amino acids (typically less than 5%, more typically less than 1%) in an encoded sequence are "conservatively modified variations", where the alterations result in the substitution of an amino acid with a chemically similar amino acid.

"Expression cassette" as used herein means a DNA sequence capable of directing expression of a particular nucleotide sequence in an appropriate host cell, comprising a promoter operably linked to the nucleotide sequence of interest which is operably linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one which is naturally occurring but has been obtained in a recombinant form useful for heterologous expression. The expression of the nucleotide sequence in the expression cassette may be under the control of a constitutive promoter or of an inducible promoter which initiates transcription only when the host cell is exposed to some particular external stimulus. In the case of a multicellular organism, the promoter can also be specific to a particular tissue or organ or stage of development.

The term "vector" as used herein refers to a construction comprised of genetic material designed to direct transformation of a targeted cell. A vector contains multiple genetic elements positionally and sequentially oriented, i.e., operatively linked with other necessary elements such that the nucleic acid in a nucleic acid cassette can be transcribed and when necessary, translated in the transformed cells. "Vector" is defined to include, inter alia, any plasmid, cosmid, phage or *Agrobacterium* binary vector in double or single stranded linear or circular form which may or may not be self transmissible or mobilizable, and which can transform prokaryotic or eukaryotic host either by integration into the cellular genome or exist extrachromosomally (e. g. autonomous replicating plasmid with an origin of replication). Specifically included are shuttle vectors by which is meant a DNA vehicle capable, naturally or by design, of replication in two different host organisms, which may be selected from actinomycetes and related species, bacteria and eukaryotic (e. g. higher plant, mammalian, yeast or fungal cells). Preferably the nucleic acid in the vector is under the control of, and operably linked to, an appropriate promoter or other regulatory elements for transcription in a host cell such as a microbial, e. g. bacterial, or plant cell. The vector may be a bi-functional expression vector which functions in multiple hosts. In the case of genomic DNA, this may contain its own promoter or other regulatory elements and in the case of cDNA this may be under the control of an appropriate promoter or other regulatory elements for expression in the host cell.

"Cloning vectors" typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector.

A "transgenic plant" is a plant having one or more plant cells that contain an expression vector.

"Plant tissue" includes differentiated and undifferentiated tissues or plants, including but not limited to roots, stems, shoots, leaves, pollen, seeds, tumor tissue and various forms of cells and culture such as single cells, protoplast, embryos, and callus tissue. The plant tissue may be in plants or in organ, tissue or cell culture.

The term "plant," as used herein, refers to any type of plant. The inventors have provided below an exemplary description of some plants that may be used with the invention. However, the list is provided for illustrative purposes only and is not limiting, as other types of plants will be known to those of skill in the art and could be used with the invention.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, water-melon, crenshaw, honeydew, cantaloupe), brussels sprouts, cabbage, cardoni, carrots, napa, cauliflower, okra, onions, celery, parsley, chick peas, parsnips, chicory, Chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet and fodder beet), sweet potatoes, swiss-chard, horseradish, tomatoes, kale, turnips, and spices.

Other types of plants frequently finding commercial use include fruit and vine crops such as apples, apricots, cherries, nectarines, peaches, pears, plums, prunes, quince almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pornes, melon, mango, papaya, and lychee.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts), fiber plants (cotton, flax, hemp, jute), Lauraceae (cinnamon, camphor), or plants such as coffee, sugarcane, tea, and natural rubber plants.

Especially applicable in the present invention are plants with a high biomass, such as plants that are also used in biofuel production, such as *Miscanthus*, switchgrass, poplar, eucalyptus, loblolly pine, willow, silver maple, alfalfa, *Jatropha*, and *Pongamia pinnata*.

Another economically important group of plants are ornamental plants. Examples of commonly grown ornamental plants include *Alstroemeria* (e.g., *Alstoemeria brasiliensis*), aster, azalea (e.g., *Rhododendron* sp.), begonias (e.g., *Begonia* sp.), bellflower, bouganvillea, cactus (e.g., *Cactaceae schlumbergera truncata*), camellia, carnation (e.g., *Dianthus caryophyllus*), chrysanthemums (e.g., *Chrysanthemum* sp.), clematis (e.g., *Clematis* sp.), cockscomb, columbine, cyclamen (e.g., *Cyclamen* sp.), daffodils (e.g., *Narcissus* sp.), false cypress, freesia (e.g., *Freesia refracta*), geraniums, gerberas, gladiolus (e.g., *Gladiolus* sp.), holly, hibiscus (e.g., *Hibiscus rosasanensis*), hydrangea (e.g., *Macrophylla hydrangea*), juniper, lilies (e.g., *Lilium* sp.), magnolia, miniroses, orchids (e.g., members of the family Orchidaceae), petunias (e.g., *Petunia hybrida*), poinsettia (e.g., *Euphorbia pulcherima*), primroses, rhododendron, roses (e.g., *Rosa* sp.), snapdragons (e.g., *Antirrhinum* sp.), shrubs, trees such as forest (broad-leaved trees and evergreens, such as conifers) and tulips (e.g., *Tulipa* sp.).

The term "plant part", as used herein, includes reference to, but is not limited to, single cells and tissues from microspores, pollen, ovules, leaves, embryos, roots, root tips, anthers, flowers, fruits, seeds, stems, shoots, scions, rootstocks, protoplasts, calli, meristematic tissues and the like.

The term "crop plant", as used herein, refers to a plant which is harvested or provides a harvestable product.

The terms "seedling" and "plantlet", as used herein, are interchangeable and refer to the juvenile plant grown from a sprout, embryo or a germinating seed and generally include any small plants showing well developed green cotyledons and root elongation and which are propagated prior to transplanting in the ultimate location wherein they are to mature.

The term "tissue culture", as used herein, refers to a culture of plant cells wherein the cells are propagated in a nutrient medium under controlled conditions.

"Significant increase" is an increase that is larger than the margin of error inherent in the measurement technique, preferably an increase by about 10%-50%, or even 2-fold or greater.

"Significantly less" means that the decrease is larger than the margin of error inherent in the measurement technique, preferably a decrease by about 2-fold or greater.

The term "endogenous" as in "endogenously produced" refers to produced within the plant (cell).

The term "production area", as used herein, refers to a location where plants are grown and where products in the form of plants or plant parts are produced for harvest. The size of the production area is generally expressed in square meters or acres of land. A production area can be an open field or a greenhouse.

The term "biomass production", as used herein, refers to the production of plant derived organic material.

The term "dry matter content", as used herein, refers to the mass fraction (%) that remains after the water fraction (%) has been removed by drying.

DNA Sequences for Transformation

Virtually any DNA composition may be used for delivery to recipient plant cells, to ultimately produce fertile transgenic plants in accordance with the present invention. For example, DNA segments in the form of vectors and plasmids, or linear DNA fragments, in some instances containing only the DNA element to be expressed in the plant, and the like, may be employed. The construction of vectors which may be employed in conjunction with the present invention will be known to those of skill of the art in light of the present disclosure (see, e. g., Sambrook et al., 1989; Gelvin et al., 1990). Vectors, including plasmids, cosmids, YACs (yeast artificial chromosomes), BACs (bacterial artificial chromosomes) and DNA segments for use in transforming cells, according to the present invention will, of course, comprise the cDNA, gene or genes necessary for production of isoprene in the transformant.

The vector of the invention can be introduced into any plant. The genes and sequences to be introduced can be conveniently used in expression cassettes for introduction and expression in any plant of interest. Such expression cassettes will comprise a transcriptional initiation region (a promoter) linked to the gene encoding the isoprene synthase gene of interest. Such an expression cassette is preferably provided with a plurality of restriction sites for insertion of the gene of interest to be under the transcriptional regulation of the regulatory regions, such as the designated promoter. The expression cassette may additionally contain selectable marker genes suitable for the particular host organism.

The transcriptional cassette will include in the 5'-to-3' direction of transcription, transcriptional and translational initiation regions, a DNA sequence of interest, and transcriptional and translational termination regions functional in plants.

The termination region may be native with the transcriptional initiation region, may be native with the DNA sequence of interest, or may be derived from another source.

Convenient termination regions are available from the Ti-plasmid of *A. tumefaciens*, such as the octopine synthase and nopaline synthase termination regions. See also, Guerineau et al. (1991) Mol. Gen. Genet. 262: 141-144; Proudfoot (1991) Cell 64: 671-674; Sanfacon et al. (1991) Genes Dev. 5: 141-149; Mogen et al. (1990) Plant Cell 2: 1261-1272; Munroe et al. (1990) Gene 91: 151-158; Ballas et al.

(1989) Nucleic Acids Res. 17: 7891-7903; Joshi et al. (1987) Nucleic Acid Res. 15: 9627-9639.

Methodologies for the construction of plant transformation constructs are described in the art.

In one embodiment of the invention, plants are transformed with the nucleotide coding for bZIP19 or bZIP23. These genes can be derived from *Arabidopsis*. Alternatively, orthologs of bZIP19 and bZIP23 may be used, such as those from *Populus trichocarpa* (PtrbZIP38 or XM_002305485.1 and PtrbZIP39 or XM_002313671.1); rice (OsbZIP48 or AK071639.1), *Helianthus annuus* (CD852649.1), *Medicago truncatula* (TA25329_3880). *Solanum tuberosum* (TA33339_3880), *Glycine max* (TA50226_3847; TA50224_3847), *Sorghum bicolor* (TA23717_4558), *Zea mays* (TA111061_4577; TA111059_4577; C0451643), or *Hordeum vulgare* (TA45897_4513).

The amino acid sequences of the *Arabidopsis* proteins are provided in FIG. 1, the genes for these proteins can be found in the gene databases under Accession No's At4g35040 or NM_119670.4 (bZIP19) and At2g16770 or NM_119670.4 (bZIP23). The sequences are also listed as SEQ ID NO: 2 and SEQ ID NO: 1, respectively. All bZIP proteins contain a characteristic and highly conserved basic domain, which binds DNA, and a leucine zipper dimerization motif. bZIPs can form homo and/or heterodimers, which bind DNA in a sequence-specific manner and are capable of binding short palindromic or pseudo-palindromic target sequences (Fyjii., Y. et al., 2000, Nature 7:889-893). Plant bZIPs are important for the regulation of pathogen defence, environmental signalling and development, but so far no function is assigned to about two thirds of the bZIP members (Hakoby, M. et al., 2002, Trends Plant Sci. 7:106-111). Among these are the bZIP19 and bZIP23 genes. They belong to group F, one of ten groups in which this family is divided. This group contains a third member, bZIP24, not identified in the yeast-one-hybrid assay. bZIP19 and bZIP23 predicted protein sequences share 69% of amino acid sequence identity and only 28 and 32%, respectively, with bZIP24. All three members of the F group contain two characteristic histidine-rich motifs (FIG. 1).

As can be seen, bZIP19 and bZIP23 share the bZIP domain at amino acid 79-110 (bZIP23) and amino acid 94-125 (bZIP19) and two histidine-rich motifs at amino acid 36-48 and 51-60 (bZIP23) and amino acid 44-56 and 59-68 (bZIP19).

Although it is possible to obtain overexpression of either bZIP19 or bZIP23 in a plant by providing such a plant with the above mentioned nucleotide sequences, a preferred embodiment of the invention is a plant in which both proteins are overexpressed. As is exemplified in the experimental part, the genes act redundantly, with bZIP19 only being partially redundant. bZIP transcription factors generally act as dimers. Their redundancy suggests that bZIP19 and bZIP23 act as homo(di)mers, in line with previous predictions (Deppmann, C. D. et al., 2006, Mol. Biol. Evol. 23:1480-1492).

Overexpression of bZIP19 and/or bZIP23 can be achieved by insertion of one or more than one extra copy of the selected gene. It is not unknown for plants or their progeny, originally transformed with one or more than one extra copy of a nucleotide sequence to exhibit overexpression.

Obtaining sufficient levels of transgene expression in the appropriate plant tissues is an important aspect in the production of genetically engineered crops. Expression of heterologous DNA sequences in a plant host is dependent upon the presence of an operably linked promoter that is functional within the plant host. Choice of the promoter sequence will determine when and where within the organism the heterologous DNA sequence is expressed. The proteins of the current invention are preferably expressed in the roots, where Zn is taken up from the soil and transported, and in other cells of the plant that are currently involved in transport and accumulation of zinc. Such root-specific promoters are well known to a person skilled in the art and can be chosen from the the RolD, RPL16A. Tub-1, ARSK1, PsMT$_a$ (WO97/20057), and Ataol promoter (Møller, S. G. and McPherson, M. J., 1998, The Plant J., 13:781-791), the AAP6 promoter (Okumoto, S. et al., 2002, J. Biol. Chem. 277:54338-54346), the tobacco RB7 promoter (Yamamoto, Y. T. et al., 1991, Plant Cell 3:371-382.), the *Arabidopsis* ADH promoter (McKendree, W. L. et al., 1992, Plant Mol Biol. 19:859-862), the *Arabidopsis* PHT1 promoter (Koyama, T. et al., 2004, J. Biosci. Bioeng. 99:38-42), the *Arabidopsis* pyk10 promoter (Nitz, I. et al., 2001, Plant Sci. 161:337-346), the peroxidase gene promoter (prxEa) of *Arabidopsis* (Wanapu and Shinmyo, 1996, Ann N. Y. Acad. Sci. 782: 107-114), the tomato SIREO promoter (Jones, M. O. et al., 2008, Funct. Plant Biol. 35:1224-1233), the alfalfa MsPRP2 promoter (Winicov, I. et al.), the rice ZRP3 and ZRP4 promoters, the maize RCc2 and RCc3 promoters, the strawberry FaRB7 promoter (Vaughan, S. P. et al., 2006, J. Exp. Botany doi: 10.1093/jxb/er1185) the promoters as disclosed in U.S. Pat. Nos. 5,459,252, 5,837,876, WO 97/005261, WO 2001/53502, WO2001/044454, WO 2006/024291 and WO 2006/022467. Alternatively, promoters can be used from genes that are normally controlled in expression by bZIP19 or bZIP23, for example those as listed in Table 3. It is believed that these promoters are especially preferable since they are expressed in the cells where the proteins normally act and since they will be induced by the presence of Zn and thus they will amplify the Zn deficiency signal causing an earlier and particularly stronger response.

Although it is known that some transgenic approaches do indeed influence adaptation of plants to changes in the zinc concentrations in the environment, these approaches are all attempts to makes plants transgenic for zinc transporter proteins (such as ZAT, see van der Zaal, B. J., 1999, Plant Physiol. 119:1047-1055; AtHMA4, see Verret, F. et al., 2004, FEBS Lett 576:306-312; and NAS, see Takahashi, M. et al., 2003, Plant Cell 15:1263-1280). The current invention attempts to interfere with the regulation of zinc, uptake, transport and storage in the plant, by modulating the expression of genes that are regulators of, amongst others, these transport proteins. Thus, the invention interferes at a more basal level, which has the advantage that it is less influenced by feedback mechanisms and other regulatory processes involved in zinc processing.

Although it is demonstrated in the experimental part that bZIP19 and bZIP23 play a major role in the control of adaptation to changes in the zinc content of the soil and although transforming plants with either or both of those proteins would make the plants able to adapt to Zn deficiency or to act as Zn (hyper)accumulators, these properties can be enhanced by overexpressing additional proteins that are known to be involved in Zn homeostasis. These proteins are preferably chosen from heavy metal transporters, preferably HMA2, HMA3 or HMA4, YSL proteins, preferably YSL, preferably YSL1 or YSL3, ZIP or IRT proteins, ZIF proteins, NAS proteins, MRP proteins, FRD3 and MTPs (metal transporting proteins).

As can be seen in this Table, genes encoding these proteins are available to the person skilled in the art and transformation of the sequences coding for these genes can be performed according to the methods as described herein.

TABLE A

Proteins involved in Zn uptake, transport and storage

| Name | Description | Acc. No. Gene | Acc. No. Protein |
| --- | --- | --- | --- |
| HMA2 | cadmium-transporting ATPase | NM_119157.3 | NP_194740.1 |
| HMA3 | potential Zn/Cd heavy metal transporter | AY434729.1 | AAR10768.1 |
| HMA4 | cadmium ion transmembrane transporter/cadmium-transporting ATPase/zinc ion transmembrane transporter | NM_127468.4 | NP_179501.1 |
| YSL1 | Oligopeptide transporter | NM_118544.3 | NP_567694.2 |
| YSL2 | Oligopeptide transporter | NM_122346.3 | NP_197826.2 |
| YSL3 | Oligopeptide transporter | NM_124735.2 | NP_200167.2 |
| ZIP1 | zinc ion transmembrane transporter | NM_112111.3 | NP_187881.1 |
| ZIP2 | zinc ion transmembrane transporter | NM_125344.2 | NP_200760.1 |
| ZIP3 | zinc ion transmembrane transporter | NM_128786.3 | NP_180786.1 |
| ZIP4 | copper ion transmembrane transporter | NM_100972.4 | NP_172566.2 |
| ZIP5 | metal ion transmembrane transporter | NM_202033.1 | NP_973762.1 |
| ZIP6 | metal ion transmembrane transporter | NM_128563.1 | NP_180569.1 |
| ZIP7 | metal ion transmembrane transporter | NM_126440.2 | NP_178488.1 |
| ZIP8 | zinc ion transmembrane transporter | NM_001161290.1 | NP_001154762.1 |
| ZIP9 | zinc ion transmembrane transporter | NM_119456.1 | NP_195028.1 |
| ZIP10 | zinc ion transmembrane transporter | NM_102864.2 | NP_174411.2 |
| ZIP11 | metal ion transmembrane transporter | NM_104468.2 | NP_564703.1 |
| ZIP12 | zinc ion transmembrane transporter | NM_125609.1 | NP_201022.1 |
| IRT3 | metal ion transmembrane transporter | NM_104776.4 | NP_564766.1 |
| ZIF1 | carbohydrate transmembrane transporter | NM_121377.4 | NP_196878.2 |
| NAS1 | nicotianamine synthase | NM_120577.3 | NP_196114.1 |
| NAS2 | nicotianamine synthase | NM_124990.1 | NP_200419.1 |
| NAS3 | nicotianamine synthase | NM_100794.3 | NP_172395.1 |
| NAS4 | nicotianamine synthase | NM_104521.2 | NP_176038.1 |
| MRP3 | glutathione S-conjugate-exporting ATPase | NM_112147.2 | NP_187915.1 |
| FRD3 | antiporter/transporter | NM_111683.1 | NP_187461.1 |
| MTP1 | zinc ion transmembrane transporter | NM_180128.2 | NP_850459.1 |
| MTP2 | | NM_116059.2 | NP_191753.1 |
| MTP3 | zinc ion transmembrane transporter | NM_115743.3 | NP_191440.2 |
| MTP8 | metal tolerance protein | NM_115668.2 | NP_191365.2 |

(Over)expression of bZIP19 and/or bZIP23 in plants together with one or more of the above mentioned proteins would yield plants which would be able to uptake more zinc than a normal wild-type plant or to respond faster to local deficiencies in zinc supply. By these characteristics, such plants would be very suitable to grow on high zinc containing soil and would therefore be able to act as phytoremediators, clearing the soil from the toxic metal, or they would be able to grow on normal or low zinc containing soil, but still have dietarily sufficient amounts of zinc in their edible parts, or be less sensitive to zinc deficiencies.

Vectors for use in tissue-specific targeting of genes in transgenic plants will typically include tissue-specific promoters and may also include other tissue-specific control elements such as enhancer sequences.

Additionally, vectors may be constructed and employed in the intracellular targeting of a specific gene product within the cells of a transgenic plant. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed. Transit or signal peptides act by facilitating the transport of proteins through intracellular membranes, e. g., vacuole, vesicle, plastid and mitochondrial membranes, whereas signal peptides direct proteins through the extracellular membrane.

A particular example of such a use concerns the direction of a protein (enzyme) to a particular organelle such as the vacuole rather than to the cytoplasm. Signal peptides of vacuolar proteins, such as the N-terminal propeptide (NTPP) of sweet potato sporamin and the C-terminal propeptide (CTPP) of tobacco chitinase can be used to target expression of a protein to the vacuole.

By facilitating the transport of the protein into compartments inside the cell, these transit peptides may increase the accumulation of gene product by protection from proteolytic degradation.

Production and Characterization of Stably Transformed Plants

Plant species may for instance be transformed by the DNA-mediated transformation of plant cell protoplasts and subsequent regeneration of the plant from the transformed protoplasts in accordance with procedures well known in the art.

Any plant tissue capable of subsequent clonal propagation, whether by organogenesis or embryogenesis, may be transformed with a vector of the present invention. The term "organogenesis", as used herein, means a process by which shoots and roots are developed sequentially from meristematic centers; the term "embryogenesis", as used herein, means a process by which shoots and roots develop together in a concerted fashion (not sequentially), whether from somatic cells or gametes. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e. g., apical meristems, axillary buds, and root meristems), and induced meristem tissue (e. g., cotyledon meristem and ultilane meristem).

Plants of the present invention may take a variety of forms. The plants may be chimeras of transformed cells and non-transformed cells; the plants may be clonal transformants (e. g., all cells transformed to contain the expression cassette); the plants may comprise grafts of transformed and untransformed tissues (e. g., a transformed root stock grafted to an untransformed scion in citrus species). The transformed plants may be propagated by a variety of means, such as by clonal propagation or classical breeding techniques. For example, first generation (or T1) transformed plants may be selfed to give homozygous second generation (or T2) transformed plants, and the T2 plants further propagated through classical breeding techniques. A dominant selectable marker (such as npt II) can be associated with the expression cassette to assist in breeding.

Thus, the present invention provides a transformed (transgenic) plant cell, in planta or ex planta, including a transformed plastid or other organelle, e. g., nucleus, mitochondria or chloroplast.

Transformation of plants can be undertaken with a single DNA molecule or multiple DNA molecules (i. e., co-transformation), and both these techniques are suitable for use with the expression cassettes of the present invention. Numerous transformation vectors are available for plant transformation, and the expression cassettes of this invention can be used in conjunction with any such vectors. The selection of vector will depend upon the preferred transformation technique and the target species for transformation.

Suitable methods of transforming plant cells include, but are not limited to, microinjection (Crossway et al., 1986), electroporation (Riggs et al., 1986), Agrobacterium-mediated transformation (Hinchee et al., 1988), direct gene transfer (Paszkowski et al., 1984), and ballistic particle acceleration using devices available from Agracetus, Inc., Madison, Wis. And BioRad, Hercules, Calif. (see, for example, Sanford et al., U.S. Pat. No. 4,945,050; and McCabe et al., 1988). Also see, Weissinger et al., 1988; Sanford et al., 1987 (onion); Christou et al., 1988 (soybean); McCabe et al., 1988 (soybean); Datta et al., 1990 (rice); Klein et al., 1988 (maize); Klein et al., 1988 (maize); Klein et al., 1988 (maize); Fromm et al., 1990 (maize); and Gordon-Kamm et al., 1990 (maize); Svab et al., 1990 (tobacco chloroplast); Koziel et al., 1993 (maize); Shimamoto et al., 1989 (rice); Christou et al., 1991 (rice); European Patent Application EP 0 332 581 (orchardgrass and other Pooideae); Vasil et al., 1993 (wheat); Weeks et al., 1993 (wheat). In one embodiment, the protoplast transformation method for maize is employed (European Patent Application EP 0 292 435, U.S. Pat. No. 5,350,689).

It is particularly preferred to use the binary type vectors of Ti and Ri plasmids of *Agrobacterium* spp. Ti-derived vectors transform a wide variety of higher plants, including monocotyledonous and dicotyledonous plants, such as soybean, cotton, rape, tobacco, and rice (Pacciotti et al., 1985: Byrne et al., 1987; Sukhapinda et al., 1987; Park et al., 1985: Hiei et al., 1994). The use of T-DNA to transform plant cells has received extensive study and is amply described (EP 120516; Hoekema, 1985; Knauf, et al., 1983; and An et al., 1985). For introduction into plants, the chimeric genes of the invention can be inserted into binary vectors as described in the examples.

Other transformation methods are available to those skilled in the art, such as direct uptake of foreign DNA constructs (see EP 0295959), techniques of electroporation (Fromm et al., 1986) or high velocity ballistic bombardment with metal particles coated with the nucleic acid constructs (Kline et al., 1987, and U.S. Pat. No. 4,945,050). Once transformed, the cells can be regenerated by those skilled in the art. Of particular relevance are the methods to transform foreign genes into commercially important crops, such as rapeseed (De Block et al., 1989), sunflower (Everett et al., 1987), soybean (McCabe et al., 1988; Hinchee et al., 1988; Chee et al., 1989; Christou et al., 1989; EP 301749), rice (Hiei et al., 1994), and corn (Gordon Kamm et al., 1990; Fromm et al., 1990).

Those skilled in the art will appreciate that the choice of method might depend on the type of plant, i. e., monocotyledonous or dicotyledonous.

*Agrobacterium tumefaciens* cells containing a vector comprising an expression cassette of the present invention, wherein the vector comprises a Ti plasmid, are useful in methods of making transformed plants. Plant cells are infected with an *Agrobacterium tumefaciens* as described above to produce a transformed plant cell, and then a plant is regenerated from the transformed plant cell. Numerous *Agrobacterium* vector systems useful in carrying out the present invention are known. These typically carry at least one T-DNA border sequence and include vectors such as pBIN19 (Bevan, 1984).

Methods using either a form of direct gene transfer or *Agrobacterium*-mediated transfer usually, but not necessarily, are undertaken with a selectable marker which may provide resistance to an antibiotic (e. g., kanamycin, hygromycin or methotrexate) or a herbicide (e. g., phosphinothricin). The choice of selectable marker for plant transformation is not, however, critical to the invention.

General methods of culturing plant tissues are provided for example by Maki et al., (1993); and by Phillips et al. (1988).

After transformation the transgenic plant cells are placed in an appropriate selective medium for selection of transgenic cells which are then grown to callus. Shoots are grown from callus and plantlets generated from the shoot by growing in rooting medium. The particular marker used will allow for selection of transformed cells as compared to cells lacking the DNA which has been introduced.

To confirm the presence of the transgenes in transgenic cells and plants, a variety of assays may be performed. Such assays include, for example, "molecular biological" assays well known to those of skill in the art, such as Southern and Northern blotting, in situ hybridization and nucleic acid-based amplification methods such as PCR or RT-PCR; "biochemical" assays, such as detecting the presence of a protein product, e.g., by immunological means (ELISAs and Western blots) or by enzymatic function.

The invention further provides a transgenic plant transformed with a nucleotide sequence coding for a bZIP19 or a bZIP23 protein or both. Additionally, said plant may be transgenic for a protein selected from the group consisting of heavy metal transporters, preferably HMA2, HMA3 or HMA4, YSL proteins, preferably YSL, preferably YSL1 or YSL3, ZIP or IRT proteins, ZIF proteins, NAS proteins, MRP proteins, FRD3 and MTPs.

As will be shown in the Examples, the transgenic plants according to the invention are tolerant to Zn deficiency, i.e. they are able to adapt to environmental situations in which there is no or hardly no zinc in the substrate on which the plant is growing. Further advantage of the transgenic plants of the current invention is that they are able to accumulate Zn. This is not only an advantage for bioremediation, but in cases of plants where Zn is stored in edible parts (such as leaves, roots, beets, berries or tubers) the plants will be suitable for diets in areas where the Zn concentration in the food is insufficient in the normal diet. This use is also known under the name of 'biofortification'. Normally the Zn in the plant will be less bioavailable because part of it is complexed with phytate or polyphenols. Thus preferably the plants used in this respect are plants that comprise low levels of phyate or and/or polyphenoles.

On the other hand, the transgenic plants of the invention are very useful in circumstances where there is an excess of zinc in the substrate. The transgenic plants of the inventions are capable of taking up the metal and storing it in their tissues and/or vacuole. In this way, the plants can be used as sanitation plants to extract zinc from the soil. The metal thus will be concentrated in the plant biomass, which can be harvested and disposed off in a convenient way. This method, known as phytoremediation, is especially useful if large areas of soil are contaminated with zinc (such as is the case in the neighbourhood of zinc mines). In such a case, phytoremediation is a commercially very attractive way of cleaning the surroundings from excess metal.

A further part of the invention is the use of a bZIP19 and/or a bZIP23 protein or an ortholog thereof, or a nucleotide sequence enclosing for such a protein or ortholog, in the methods of the invention described above, and/or for making a plant as described above and progeny thereof.

The following enabling Examples serve to further illustrate the invention, and are not intended to define limitations or restrict the scope of the subject invention.

EXAMPLES

Example 1—Material and Methods

Plant Growth

Arabidopsis ecotype Columbia (Col-0) was used in all experiments. Plants were grown in climate chambers with 16 h light at 22° C., 8 h at 20° C., 120 µmol photons $m^{-2} s^{-1}$ and 50% relative humidity. Previous to germination, seeds had a 3-day stratification treatment in a cold room at 4° C. in the dark to promote uniform germination. For genetic analysis and transformation, plants were grown in pots with peat. For the plate-based assay, seeds were surface-sterilized using vapour-phase seed sterilization and sown on plates with MS media (Duchefa Biochemie, Haarlem, The Netherlands) supplemented with 1% sucrose and adjusted to pH 5.8. The MS media was prepared either without zinc (Zn−), with 30 µM $ZnSO_4$ (Zn+) or with 300 µM $ZnSO_4$ (Zn++). For the hydroponically grown plants, seeds were sown on 0.55% agar-filled tubes and grown on a modified half-strength Hoagland's nutrient solution prepared with either 0.05 µM (Zn−), 2 µM $ZnSO_4$ (Zn+), or 25 µM $ZnSO_4$ (Zn++). The hydroponic system consisted of 8-liter-capacity containers (46×31×8 cm), with a non-translucent 3-mm thick plastic lid containing holes for placing 9×5 agar-filled tubes. The nutrient solution was replaced once in the first week and twice in the weeks thereafter.

Yeast Complementation Experiment

A 1.3-kb full-length cDNA clone corresponding to AtZIP4 (APD09D10R, genebank accession number AV524735) was kindly provided by Kazuza DNA Research Institute (Kisarazu, Chiba, Japan). The open-reading frame of ZIP4 was amplified with proofreading DNA polymerase (Pfu native; Stratagene, La Jolla, Calif., USA), with PCR conditions as recommended by the manufacturer, and using the primers (SEQ ID NO: 5)
5'-<u>GGGGACAAGTTTGTACAAAAAAGCAGGCTT</u>AACTCTTGTTCCCATGA
TC-3'
and (SEQ ID NO: 6)
5'-<u>GGGGACCACTTTGTACAAGAAAGCTGGGTA</u>TATTATTTGATTCTACA
G-3' containing Gateway recombination sites (underlined). The fragment was cloned into the entry vector pDONR207 (Invitrogen) by in vitro site-directed recombination for further recombination into the yeast expression vector pFL613 (20). The ATG start-codon of the cloned ZIP4 cDNA was in frame with the pFL613 ATG start-codon and without stop-codons upstream. The construct was verified by sequencing.

A Saccharomyces cerevisiae zrt1zrt2 mutant, ZHY3, and its parental wild-type strain DY1457 were used (6). Yeast cells were grown on synthetic defined liquid media (SD) supplemented with auxotrophic requirements and 2% (w/v) glucose. Both yeast strains were transformed with the pFL613 empty vector, and zrt1zrt2 was transformed with pFL613 containing AtZIP4, using a standard yeast transformation procedure (21). zrt1zrt2 complementation was tested by a drop spotting assay, spotting diluted cultures from a single colony of each transformant on selective SD-URA agar plates. The media was made zinc-limiting by adding EDTA (1 mM) and citrate (pH 4.2) (22) and supplemented with 0.4 (zinc-limiting media) or 0.8 mM $ZnCl_2$. Five colonies of each transformant were tested. zrt1zrt2 complementation was also tested by measuring the $OD_{600}$ in 5-ml cultures of the described SD-URA media with 0.4 mM $ZnCl_2$ inoculated with a 60 µl (0.8 mM $ZnCl_2$) single-colony overnight pre-culture at $OD_{600}=1$. Three independent experiments were performed.

Construction of Reporter Vectors for the Yeast One-Hybrid

The bait sequence in six reporter vectors (named A to F) were PCR-amplified fragments of the ZIP4 promoter. These fragments covered the full promoter, starting −1049 bp upstream of the start codon and had an overlap between fragments of 60 to 80 bp. The fragments were amplified from Arabidopsis genomic DNA using proofreading polymerase (Pfu native; Stratagene, La Jolla, Calif., USA), with PCR conditions as recommended by the manufacturer, and using primers with 5'-overhangs compatible with EcoRI/SacI (table 1). The fragments were intermediately cloned into the pCR-Blunt II-TOPO vector (Invitrogen) according to the manufacturer's recommendations. The TOPO vector with each of the baits was digested with EcoRI/SacI and the bait fragment was extracted from agarose gel (Qiagen Gel Extraction kit). The bait of the reporter vector G consisted of a trimer of the following motif: ATGTCGACAT/C. Two antiparallel oligonucleotides, one representing the sense strand and the other its antisense complement strand, and containing 5'-overhangs compatible with EcoRI/SacI, were synthesized (table 1).

a standard yeast transformation procedure (Gietz, R. D. et al., 2002, Meth. Enzymol. 350:87-96). The empty pHISi vector, digested and undigested, and a non-integrative reporter vector were used as controls. The cDNA expression library screening was performed following the Large-Scale Yeast Transformation Protocol (PT3024-1; Clontech) which yielded a transformation efficiency of 5 to $9 \times 10^5$ cfu $\mu g^{-1}$ DNA. Screening with all the reporter strains was performed on medium lacking His and in the presence of 20-40 mM 3-aminotriazole (3AT, optimal concentration was optimized for each reporter strain). There were in total 18 positive interactions (7 with bZIP19 and 11 with bZIP23) when using the reporter vectors E, F and G (FIG. 2A). Positive colonies

TABLE 1

Forward and reverse primers used to amplify bait fragments A-F from the ZIP4 promoter, and sense and antisense complement strands used to synthesise the three-tandem repeat of the motif ATGTCGACAT/C(G), to be used as bait fragment G.

| Fragment | | Primer sequence | SEQ ID NO: |
|---|---|---|---|
| A | Forward | 5'-GAATTCAAGCTTTGGAAAGTGAAGTGGA-3' | 8 |
|   | Reverse | 5'-GAGCTCCAATTTCAAACCAGTA-3' | 9 |
| B | Forward | 5'-GAATTCTGTATATCTGATCTTCTCTGCTG-3' | 10 |
|   | Reverse | 5'-GAGCTCAAGCTAAAAGGACGGTAACT-3' | 11 |
| C | Forward | 5'-GAATTCTTCATCCTATTGCTTGG-3' | 12 |
|   | Reverse | 5'-GAGCTCATTTTCCCATTTGTTCCAC-3' | 13 |
| D | Forward | 5'-GAATTCTCTGCAGTAGACTTGAC-3' | 14 |
|   | Reverse | 5'-GAGCTCCCCAATCTTGTCTAT-3' | 15 |
| E | Forward | 5'-ATCGGAATTCGTGAGAAAACAGAATAACGC-3' | 16 |
|   | Reverse | 5'-GAGCTCCCATGGGAACAAGAGTTTAT-3' | 17 |
| F | Forward | 5'-ATCGGAATTCGTGAGAAAACAGAATAACGC-3' | 18 |
|   | Reverse | 5'-CGTAGAGCTCTGGAGAAAGAGTGAAAGAGT-3' | 19 |
| G | Forward | 5'-AATTCATGTCGACATATGTCGACATATGTCGACACGAGCT-3' | 20 |
|   | Reverse | 5'-CGTGTCGACATATGTCGACATATGTCGACATG-3' | 21 |

0.1 µg of each oligonucleotide strand were mixed in 10 µl of 50 mM NaCl, annealed by heating at 70° C. for 5 min, and slowly cooled down to room temperature. The digested, PCR-derived baits (A to F) and the annealed oligonucleotide (G), were cloned into pHISi, previously digested with EcoRI/SacI according to the manufacturer's recommendations. Each reporter vector was confirmed by digestion analysis and sequencing.

Yeast One-Hybrid Screening

The cDNA expression library was constructed with mRNA from *Arabidopsis* inflorescence obtained using an mRNA purification kit (Amersham Bioscience).

Subsequently, a Gateway compatible cDNA entry library was constructed making use of the CloneMiner cDNA library Construction Kit (Invitrogen, Carlsbad). This cDNA entry library had a titer of $5 \times 10^7$ cfu $ml^{-1}$ and it was transferred into the pDEST22 vector (Invitrogen) via an LR recombination reaction following the protocol provided by the manufacturer, yielding an expression library with a titer of $2 \times 10^6$ cfu $ml^{-1}$. The reporter vectors were introduced into yeast strain PJ69-4A (James, P. et al., 1996, Genetics 144: 1425-1436). For this purpose, yeast cells were transformed with digested (Xho1) linearized pHISi reporter vector using were selected and the cDNA clone of the GAL4-AD library vector was isolated and sequenced.

Identification of T-DNA Insertion Mutants

T-DNA SALK lines were obtained from the Nottingham *Arabidopsis* Stock Center (NASC). The T-DNA was inserted 18 bp upstream of the bZIP19 (At4g35040) start codon in m19 (salk_144252), and 91 bp upstream of the bZIP23 (At2g16770) start codon in m23 (salk_045200). The T-DNA insertion events were confirmed by PCR analysis with gene-specific primers of LP and RP described by the Salk Institute Genomic Analysis Laboratory and a T-DNA border primer LBa1. Homozygous plants for each T-DNA insertion were selected. In order to obtain a double T-DNA insertion mutant, m19m23, the progeny of a cross between m19 and m23 plants were selected by PCR analysis for homozygosity of each T-DNA insert.

Quantitative RT-PCR Analysis

Seedlings of *Arabidopsis* wild-type (wt), and T-DNA insertion mutants m19, m23 and m19m23 grown for three weeks in MS medium at either Zn−, Zn+ or Zn++ conditions were harvested. Seedlings from a single plate, per genotype and per treatment were pooled (6 to 8 seedlings) and homogenized in liquid nitrogen. For each genotype and treatment, seedlings were harvested from 3-4 different plates, representing independent experiments. Total RNA of the seedlings was extracted with an RNAeasy plant RNA kit (Qiagen) and treated with DNAse to eliminate any genomic DNA (Fermentas). The kits were used according to manufacture's instructions. First-strand cDNA was synthesized from 1 µg of total RNA using the iScript™ cDNA Synthesis Kit (Bio-Rad). Gene-specific primers for quantitative RT-PCR were designed according to database genome sequence information for *Arabidopsis* and using Vector NTI software (Invitrogen) (table 2).

TABLE 2

Forward and reverse primers used in the quantitative RT-PCR to determine transcript expression of ZIP4, ZIP1, ZIP3, ZIP5, ZIP9, ZIP12, IRT3, ZIP2, bZIP19, bZIP23 and bZIP24 genes.

| Fragment | | Primer sequence | SEQ ID NO: |
|---|---|---|---|
| ZIP4 | Forward | 5'-GATCTTCGTCGATGTTCTTTGG-3' | 22 |
| | Reverse | 5'-TGAGAGGTATGGCTACACCAGCAGC-3' | 23 |
| ZIP1 | Forward | 5'-GGACACACACATGGTTCGAC-3' | 24 |
| | Reverse | 5'-GATAGTGCAGCCATGAGTGG-3' | 25 |
| ZIP3 | Forward | 5'-CAGAAACATGTTTCTTCTTCGTCAC-3' | 26 |
| | Reverse | 5'-CGCAATAAATCCGGTGAACG-3' | 27 |
| ZIP5 | Forward | 5'-CGGGATTGTTGGCGTGGAAT-3' | 28 |
| | Reverse | 5'-CCAAGACCCTCGAAGCATTG-3' | 29 |
| ZIP9 | Forward | 5'-CAATAATCATAGGAATATCGCTTGG-3' | 30 |
| | Reverse | 5'-AGAAAGCCATCATGGCAGAT-3' | 31 |
| ZIP12 | Forward | 5'-CAATGTTGATTGAATCCTTTGC-3' | 32 |
| | Reverse | 5'-CCATGAGAATGTCCTTGTGA-3' | 33 |
| IRT3 | Forward | 5'-ATATGTTGGCGGGTGGCACG-3' | 34 |
| | Reverse | 5'-GCTTCCCTCTCTTGCTTCCG-3' | 35 |
| ZIP2 | Forward | 5'-TAATAACAACCACGTCGGAG-3' | 36 |
| | Reverse | 5'-AGCAAAGCTGTGTCTCCAAA-3' | 37 |
| bZIP19 | Forward | 5'-TTCTCCCGGATGAGAGCGATGA-3' | 38 |
| | Reverse | 5'-GCTGATTCACCGCCCTAAGCCT-3' | 39 |
| bZIP23 | Forward | 5'-TAATCAGCTGTTGAAGAGGT-3' | 40 |
| | Reverse | 5'-TCATGTATGAGTAAGGCACG-3' | 41 |
| bZIP24 | Forward | 5'-TCTCAGGATCAGCAAGAGAA-3' | 42 |
| | Reverse | 5'-TCAGTTTCCACCATTTCTTGG-3' | 43 |

Amplicon lengths were between 150 and 240 bp and all primer combinations had at least 85% efficiency. The absence of genomic DNA was confirmed by performing a no-amplification control (without reverse transcriptase reaction) for every sample. For the PCR reaction, 5 µl of a 100× dilution of the cDNAs, corresponding approximately to 2.5 ng of RNA, were used as template. In addition, the reaction contained 12.5 µl iQ™ SYBR® Green Supermix (Bio-Rad) and 5 pmol of forward and reverse primers (Invitrogen) in a total volume of 25 µl. The PCR reactions were performed in a 96-well plate with an iCycler thermal cycler and an iCycler iQ Real Time PCR System (Bio-Rad). The following standard thermal profile was used: 3 min at 95.0° C., followed by 40 cycles of 15 sec at 95.0° C. and 1 min at 60.0° C. 18S rRNA was used as an internal control, to normalize the amount of template cDNA. Reactions were performed in 3-4 biological replicas and 2-6 technical replicas per biological replica for each genotype x treatment. Relative transcript levels (RTL) were calculated with the $2^{-\Delta\Delta C_T}$ method (24).

Determination of Zinc Concentration

Roots and shoots of four-week-old hydroponically grown *Arabidopsis* wild-type (wt), T-DNA insertion mutants m19, m23 and m19m23, were harvested, consisting of three plants per genotype x three treatments (Zn−, Zn+, Zn++) x two independent experiments. The root systems were desorbed with ice-cold 5 mM $PbNO_3$ for 30 min. Roots and shoots were analyzed for zinc concentration using flame atomic absorption spectrometry (Perkin Elmer 1100B).

Generation of Constructs

To generate overexpressor constructs for transformation of the *Arabidopsis* double T-DNA insertion mutant (m19m23), full-length cDNAs of AtbZIP19 and AtbZIP23 (clones GSLTSIL54ZH09 and GSLTFB35ZE06, respectively) were obtained from the CNRGV (Centre National de Ressources Génomiques Végétales, France) in pCMV SPORT6 cloning vector, containing Gateway recombination sites. The cDNAs were cloned into the entry vector pDONR207 (Invitrogen) by in vitro site-directed recombination, for further recombination into the overexpressor vector pGD625 (De Folter, S. et al., 2005, Plant Cell 17:1424-1433). The constructs pCaMV35S::bZIP19 (OX19) and pCaMV35S::bZIP23 (OX23) were verified by digestion analysis and sequencing and transformed by electroporation into *Agrobacterium tumefaciens* strain AGL0. Subsequently, m19m23 and *Arabidopsis* wild-type plants were transformed by floral dipping (Clough, S. J. et al., 1998, Plant J. 16:735-743). Independent transformed lines were selected for a single insertion locus by antibiotic resistance and 3:1 segregation ratio of T2 seedlings. The overexpression of bZIP19 or bZIP23 was confirmed by RT-PCR. Five, respectively three independent lines of m19m23-OX19 and m19m23-OX23 were analysed with 10 seedlings per line, grown in MS medium at either Zn− or Zn+ conditions, in two replicate plates per line. *Arabidopsis* wild-type and m19m23 plants were used as controls.

Micro-Array Analysis

*Arabidopsis* wild-type (wt) and T-DNA insertion double mutant m19m23 plants were grown in hydroponics medium as described above. They were grown for three weeks with normal zinc supply (Zn+, 2 µM ZnSO$_4$) and one week with low zinc supply (Zn−, 0.05 µM ZnSO$_4$) or normal zinc supply (Zn+). Roots of four plants per genotype and per treatment (Zn−/Zn+) were pooled in a two biological replica experiment, and RNA was extracted with the RNAeasy plant RNA kit (Qiagen). Transcriptomes were analysed using 1 µg of total RNA as starting material. Targets were prepared with the one-cycle cDNA synthesis kit followed by biotin-labelling with the IVT labelling kit (GeneChip One-cycle target labelling and control reagents, Affymetrix, High Wycombe, U.K.) and hybridized to ATH1 gene chip for 16 h as recommended by the supplier (Gene expression analysis manual, Affymetrix). Raw data files were processed and quantile normalized in Bioconductor/R (27). Differential expression of each gene was tested for by applying an Empirical Bayes regularized t-test (Smyth, G. K., 2004, Stat. Appl. Genet. Mol. Biol. 3, Iss. 1, Article 3)). The p-values were corrected for multiple testing using the approach of Benjamini and Hochberg (1995, J. Royal Stat., Soc. B 57:289-300), providing control of the false discovery rate (FDR).

Statistics

Data analysis and statistics were done using Microsoft Excel and SPSS 15.0 for Windows. Statistical analysis of zinc concentration and dry weight data, from *Arabidopsis* and mutant lines, was performed by one-way ANOVA followed by a post-hoc Tukey test.

Results

Figure 3A:
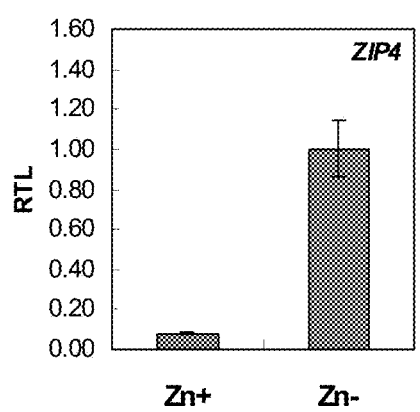
FIG. 3A-3C: Gene expression and zinc transport of the *Arabidopsis* ZIP4 zinc transporter.
Figure 3B:
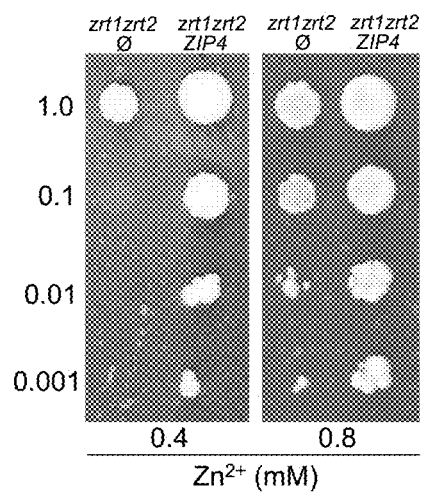
Figure 3C:
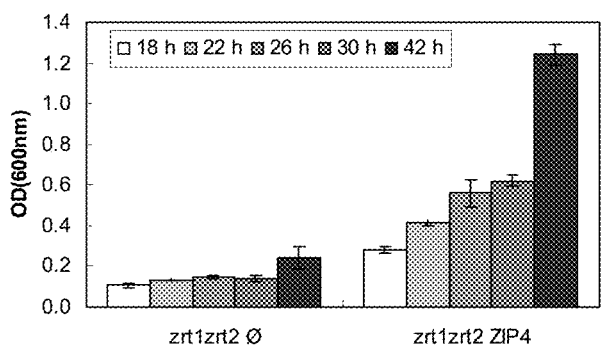

In *Arabidopsis*, several members of the ZIP family of metal transporters mainly involved in cellular uptake, are transcriptionally induced in response to zinc deficient conditions and thought to constitute the major gateway of zinc into the plant. The ZIP4 gene in particular is strongly induced in roots upon zinc deficiency (FIG. 3A). We used it to complement the increased zinc requirement of the *Saccharomyces cerevisiae* zrt1zrt2 mutant defective in high- and low-affinity zinc uptake (Zhao, H. et al., 1996, Proc. Natl. Acad. Sci. USA 93:2454-2458)), and showed it indeed encodes a zinc transporter (FIGS. 4, B and C). We cloned the promoter of the ZIP4 gene upstream of the GUS reporter gene and expressed this construct in *Arabidopsis*. GUS expression was apparent only when plants were grown on zinc deficient medium, analogous to endogenous ZIP4 gene expression (data not shown). To identify transcription factors controlling ZIP4 expression, we used six overlapping ZIP4 promoter fragments as baits in a yeast-one-hybrid assay. We also used three tandem repeats of a 10-bp palindrome motif, present in two copies close to the predicted ZIP4 transcription start, as additional bait (FIG. 2A; fragments A to G). Several clones of two cDNAs were identified, but only when screening with baits containing two or three copies of the 10-bp palindrome (FIG. 2A; fragments E, F and G). These cDNAs corresponded to bZIP19 (At4g35040, NM_119670.4) and bZIP23 (At2g16770, NM_119670.4), two genes of the basic region/leucine zipper motif (bZIP) family of transcription factors. *Arabidopsis* contains 75 members of the bZIP family (Jakoby, M. et al., 2002, Trends Plant Sci. 7:106-111).

Figure 2B:
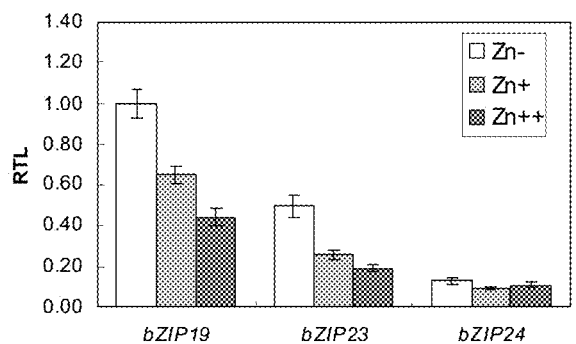

To investigate the involvement of these three bZIP genes in controlling adaptation of plants to low zinc supply, we analysed transcript levels by quantitative RT-PCR (qPCR) on three-week-old wild-type seedlings grown on agar plates at three different zinc concentrations. Expression of bZIP19 and bZIP23 genes decreased to about half upon increased zinc supply, with bZIP19 slightly higher expressed than bZIP23 (FIG. 2B). bZIP24 had lower transcript levels than the other two, and expression was not obviously affected by the zinc status of the medium, therefore we concluded that bZIP19 and bZIP23 are involved in the response to zinc deficiency in plants.

Figure 4C:
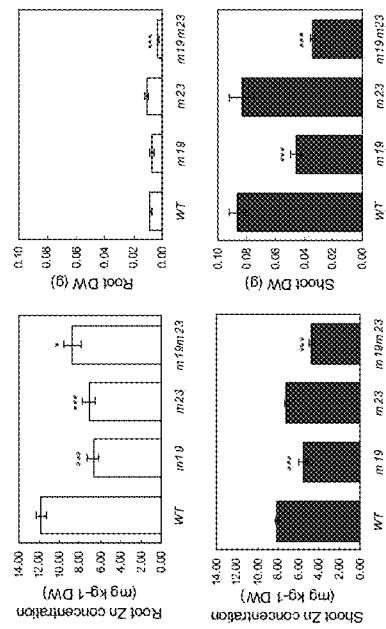
FIG. 4A-4C: The double T-DNA insertion mutant m19m23 is hypersensitive to zinc deficiency.
Figure 4A:
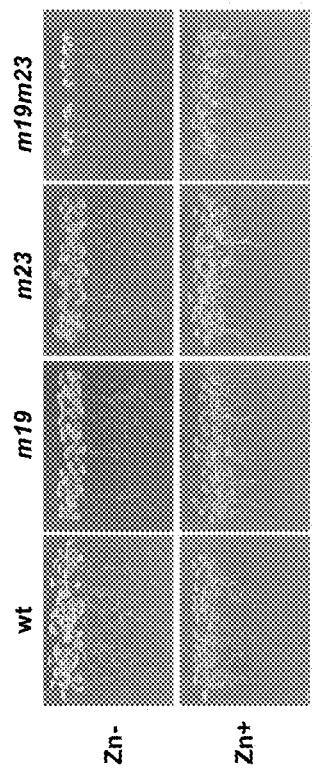
Figure 4B:
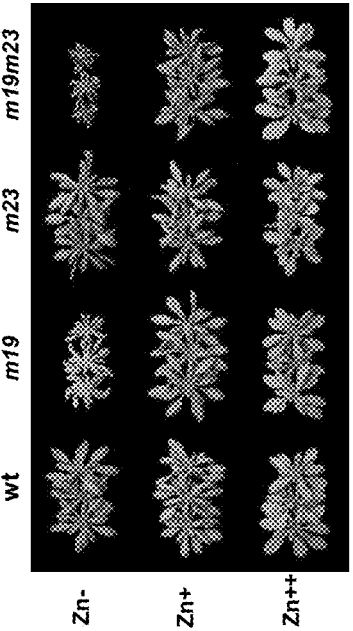
Figure 5A:
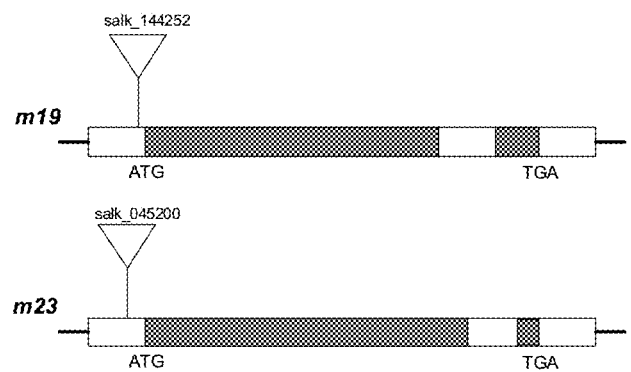
FIG. 5A-5B.
Figure 5B:
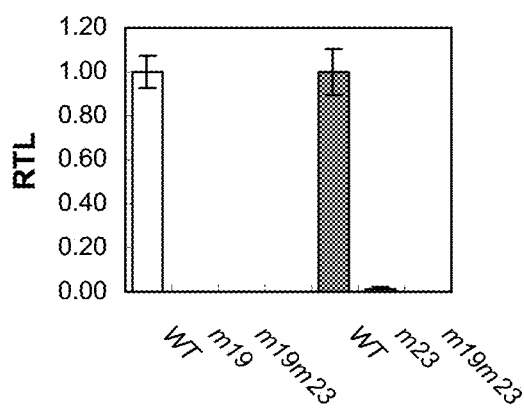
Figure 6:
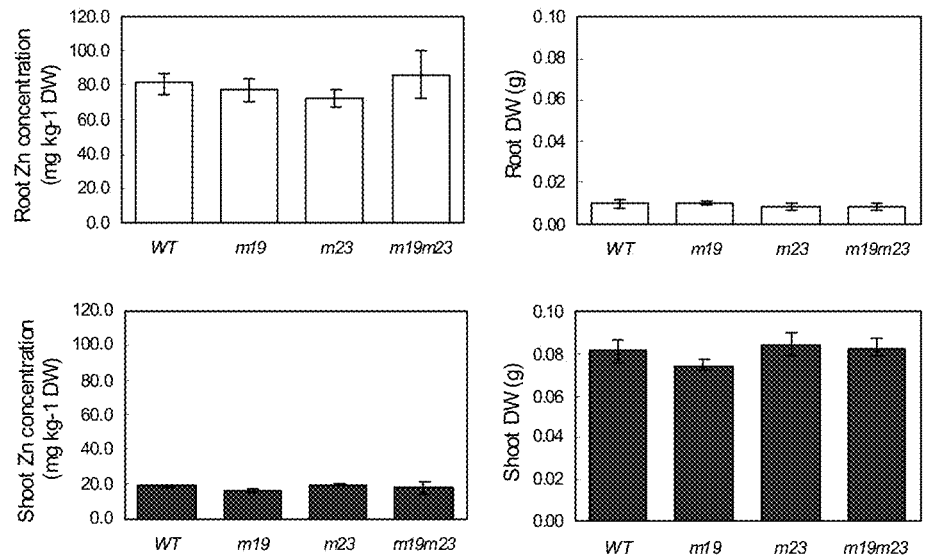
FIG. 6: Zinc concentration (in mg kg$^{-1}$ dry weight) and dry weight (DW; in g) of roots (white bars) and shoots (grey bars) of 4-week-old wild-type (WT), bZIP19 (m19) and bZIP23 (m23) single mutants and double mutants (m19m23), grown in hydroponics at 2 μM ZnSO$_4$ (Zn+). Error bars indicate SE.
Figure 7:
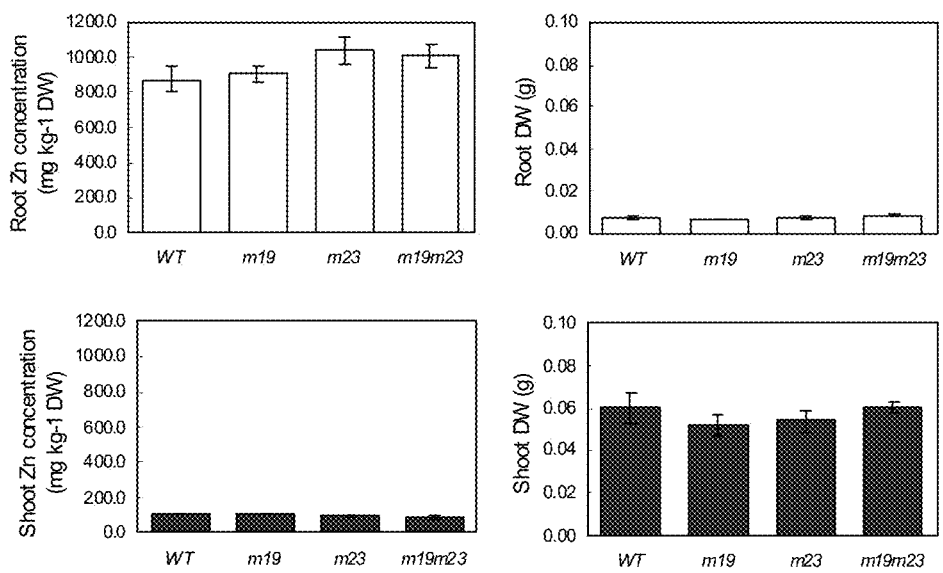
FIG. 7: Zinc concentration (in mg kg$^{-1}$ dry weight) and dry weight (DW; in g) of roots (white bars) and shoots (grey bars) of 4-week-old wild-type (WT), bZIP19 (m19) and bZIP23 (m23) single mutants and double mutants (m19m23), grown in hydroponics at 25 μM ZnSO$_4$ (Zn+). Error bars indicate SE.
Figure 8A:
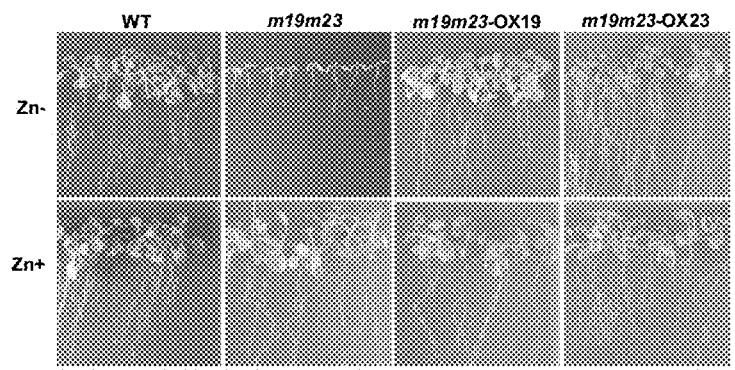
FIG. 8A-8B: Complementation study and expression analysis of putative target genes.

To determine their mutant phenotypes, we obtained homozygous T-DNA insertion lines for the bZIP19 and bZIP23 genes (respectively named m19 and m23) which were devoid of full-length bZIP19 or bZIP23 transcript (FIGS. 5, A and B). We crossed both single mutant lines to generate a double mutant line (m19m23). Wild type plants and single or double mutants grown on soil did not show any obvious phenotypic differences (data not shown), however when grown on zinc-deficient agar media (Zn−), only the double mutant line was hypersensitive to zinc-deficiency (FIG. 4A). Three-week-old seedlings showed very poor growth and strong chlorosis. To exclude in vitro effects during tissue culture, we grew plants for longer time on hydroponics medium, where they could develop normally. Four-week-old double mutant plants, growing at low zinc supply (Zn−) showed a strong growth reduction compared to wild-type plants, as determined by dry weight comparison (FIGS. 4, B and C). These plants also had a decreased zinc uptake, with only 58% and 73% of the respective shoot and root zinc concentration of wild-type plants (FIG. 4C). At low zinc supply on hydroponics, also the m19 single mutant showed reduction in growth and decreased zinc uptake when compared to wild type (FIG. 4B). When growing in zinc-sufficient (Zn+) or zinc-excess media (Zn++), we did not see differences between the mutants and the wild-type (FIGS. 4, A and B), neither for zinc content nor for dry weight (FIG. 6,7). To prove that mutations in bZIP19 and bZIP23 indeed caused the phenotype of the m19m23 double mutant we expressed either the bZIP19 or the bZIP23 cDNA, each under control of the CaMV 35S promoter, in the double mutant. This fully complemented the zinc deficiency hypersensitive phenotype (FIG. 8A).

These findings show that bZIP19 and bZIP23 encode essential transcription factors that control the zinc deficiency response in plants. These genes act redundantly, with bZIP19 only being partially redundant. bZIP transcription factors generally act as dimers. Their redundancy suggests that bZIP19 and bZIP23 act as homo(di)mers, in line with previous predictions (Deppmann, C. D. et al., 2006, Mol. Biol. Evol. 23:1480-1492). The DNA target sequence for binding bZIP19 and bZIP23 should be within the 10-bp imperfect palindrome present in two copies in the ZIP4 promoter, as three tandem copies of this sequence were sufficient to identify both bZIPs in the yeast-one-hybrid assay. We therefore called the palindrome consensus sequence (RTGTCGACAY) (SEQ ID NO:44) a Zinc Deficiency Response Element (ZDRE). The ZDRE does not have the typical ACTG core as found in the A-box (TACGTA), C-box (GACGTC) or G-box (CACGTG) DNA elements, to which plant bZIPs are known to preferentially bind. Although also other binding sites have been reported (Choi, H. et al., 2000, J. Biol. Chem. 275:1723-1730; Fukazawa, I. Et al., 2000, Plant Cell 12:901-915) the ZDRE is not among them.

Figure 8B:
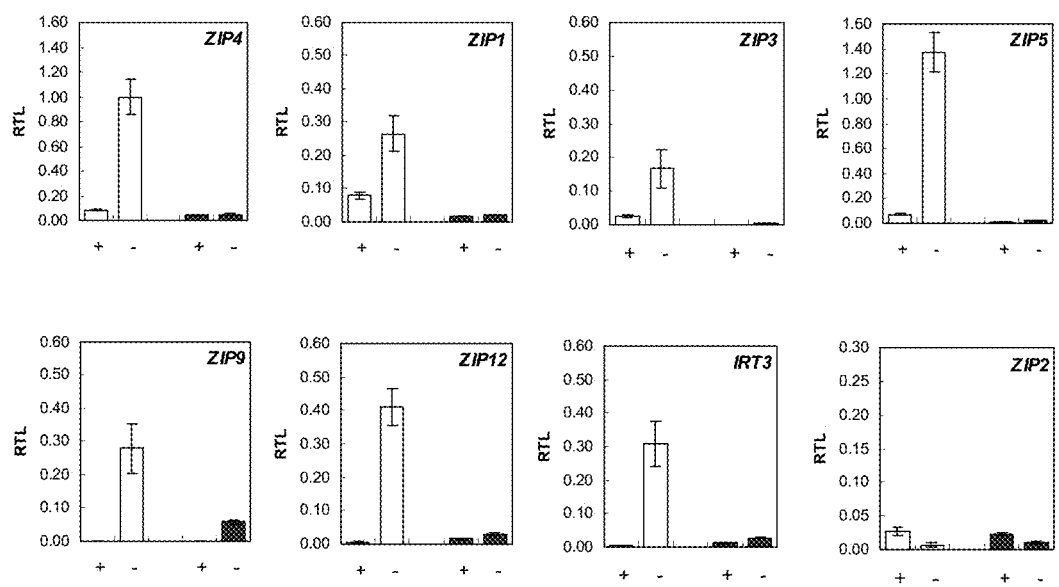

To further confirm that the ZDRE is indeed the characteristic cis element to target genes for transcriptional control by bZIP19/23, we screened the promoters of other ZIP transporter genes for ZDREs. Of the 15 *Arabidopsis* ZIP genes (Maser, P. et al., 2001, Plant Physiol. 126:1646-1667), approximately half are described to be transcriptionally induced under zinc deficiency conditions compared to normal zinc supply (Grotz, N. et al., 1998, Proc. Natl. Acad. Sci USA 95:7220-7224; Van de Mortel, J. E. et al., 2006, Plant Physiol. 142:1127-1147; Wintz, H. et al., 2003, J. Biol. Chem. 278:47644-47653). Only ZIP1, ZIP2, ZIP3, ZIP4 and IRT3 encode proteins characterized as zinc transporters (Grotz, supra; Lin, Y.-F. et al., 2009, New Phytol. 182:392-404) although others are likely to transport zinc too. ZIP1, ZIP3, ZIP4, ZIP5, ZIP9, ZIP12 and IRT3 contain one or two ZDRE copies in their promoters and these genes do not show the typical induction of expression in the m19m23 double mutant under zinc-deficient conditions as we saw in the wild-type (FIG. 8B). Expression of ZIP2, which is not zinc-deficiency induced and has no ZDRE sequence in its promoter, is not affected when comparing mutant and wild-type (FIG. 8B). In order to determine the effect of loss of bZIP19/23 function on global gene expression we performed a micro-array experiment comparing roots of hydroponically grown four-week-old m19m23 double mutant plants with those of wild-type plants, treated in their last week with low zinc supply (Zn−). Only 23 genes showed a statistically significant alteration of transcript levels exceeding a 1.5-fold difference threshold (Table 3).

Among those, 16 were down-regulated in the double mutant, including bZIP19 (a probe for bZIP23 was not included in the micro-array used). Of the 15 remaining genes, 11 are known to be induced in wild type *Arabidopsis* roots upon zinc deficiency (Van de Mortel et al., supra) and nine contain one or more copies of ZDRE in their promoter regions. We think these are the direct targets of bZIP19 and bZIP23, important for the primary zinc deficiency response, and the other genes represent a secondary effect. These findings confirm the important role of the ZDRE and the bZIP19/23 genes in controlling *Arabidopsis* zinc deficiency response. It also shows that the strong negative effect on growth and on zinc concentration of the m19m23 mutant when grown under zinc deficiency (FIGS. 4, A, B and C) is largely explained by reduction in expression of a relatively small group of zinc homeostasis genes involved in uptake and translocation of metals.

TABLE 3

Differentially expressed genes detected by comparative micro-array analysis of the root transcriptome of *Arabidopsis* wild-type and m19m23 double mutant plants. Roots of four-week old plants grown in hydroponics exposed in their last week to zinc deficiency (Zn-) were used. Fold change (FC) ≥1.5 and adjusted p-values (Benjamini-Hochberg, BH) ≤0.05 were used as cut-offs. Average expression value (log2 scale) of the gene model in the data set is indicated as A.

| Annotation (www.arabidopsis.org) | Gene Model | FC (≥1.5) | A | Adjusted p-value (BH) |
|---|---|---|---|---|
| down-regulated | | | | |
| bZIP transcription factor family protein | AT4G35040 | -35.87 | 7.31 | 9.27E-08 |
| ZIP3 (ZINC TRANSPORTER 3 PRECURSOR)* | AT2G32270 | -26.23 | 9.67 | 1.35E-09 |
| phosphatidylinositol 3- and 4-kinase family protein/ ubiquitin family protein | AT5G24240 | -8.43 | 8.20 | 3.57E-08 |
| ZIP5 (ZINC TRANSPORTER 5 PRECURSOR)* | AT1G05300 | -8.34 | 6.90 | 4.15E-07 |
| ZIP4 (ZINC TRANSPORTER 4 PRECURSOR)* | AT1G10970 | -7.19 | 7.68 | 9.27E-08 |
| ZIP9 (ZINC TRANSPORTER 9 PRECURSOR)* | AT4G33020 | -3.23 | 6.90 | 4.41E-04 |
| ZIP1 (ZINC TRANSPORTER 1 PRECURSOR)* | AT3G12750 | -3.21 | 7.33 | 1.10E-05 |
| nicotianamine synthase, putative* | AT5G56080 | -3.02 | 9.24 | 1.28E-02 |
| ATPAP27/PAP27 (purple acid phosphatase 27) | AT5G50400 | -2.51 | 9.79 | 1.10E-05 |
| nicotianamine synthase, putative* | AT1G56430 | -2.46 | 7.68 | 1.98E-03 |
| ATARP9 (ACTIN-RELATED PROTEIN 9) | AT5G43500 | -2.33 | 7.28 | 3.16E-05 |
| FRD3 (FERRIC REDUCTASE DEFECTIVE 3) | AT3G08040 | -1.78 | 8.61 | 1.98E-03 |
| prolyl oligopeptidase, putative/prolyl endopeptidase, putative/post-proline cleaving enzyme, putative* | AT1G20380 | -1.77 | 8.28 | 6.20E-03 |
| WR3 (WOUND-RESPONSIVE 3) | AT5G50200 | -1.60 | 11.63 | 2.48E-02 |
| ZIP10 (ZINC TRANSPORTER 10 PRECURSOR)* | AT1G31260 | -1.60 | 6.30 | 3.09E-02 |
| similar to unknown protein [*Arabidopsis thaliana*] (TAIR:AT1G61260.1) | AT4G04990 | -1.59 | 8.41 | 4.22E-03 |
| up-regulated | | | | |
| LAC2 (laccase 2) | AT2G29130 | 1.82 | 7.01 | 1.82E-02 |
| ANR1; DNA binding/transcription factor | AT2G14210 | 1.71 | 8.90 | 2.85E-02 |

TABLE 3-continued

Differentially expressed genes detected by comparative micro-array analysis of
the root transcriptome of Arabidopsis wild-type and m19m23 double mutant plants.
Roots of four-week old plants grown in hydroponics exposed in their last week to zinc
deficiency (Zn-) were used. Fold change (FC) ≥1.5 and adjusted p-values (Benjamini-
Hochberg, BH) ≤0.05 were used as cut-offs. Average expression value (log2 scale)
of the gene model in the data set is indicated as A.

| Annotation (www.arabidopsis.org) | Gene Model | FC (≥1.5) | A | Adjusted p-value (BH) |
|---|---|---|---|---|
| similar to unknown protein [Arabidopsis thaliana] (TAIR:AT1G21670.1) | AT1G21680 | 1.57 | 8.98 | 2.85E-02 |
| ATEBP/ERF72/RAP2.3 (RELATED TO AP23) | AT3G16770 | 1.55 | 9.68 | 4.18E-02 |
| COBL2 (COBRA-LIKE PROTEIN 2 PRECURSOR) | AT3G29810 | 1.54 | 7.40 | 3.42E-02 |
| kelch repeat-containing F-box family protein | AT1G80440 | 1.52 | 11.05 | 9.48E-03 |
| ATPSK2 (PHYTOSULFOKINE 2 PRECURSOR) | AT2G22860 | 1.52 | 9.20 | 4.24E-02 |

*Indicates genes that contain one or more copies of the ZDRE in their promoter region.

In summary, the bZIP19 and bZIP23 transcription factor function is essential for the response and adaptation of plants to low zinc supply. The identification of these transcription factors, as well as the ZDRE element they bind to and the target genes they regulate, constitutes an important step forward towards a full understanding of zinc homeostasis in plants.

Example 2

Arabidopsis plants, accession Col, were transformed with OX19 or OX23 (for the construction of these vectors, see Example 1) and homozygous T3 plants were obtained. Three high expressing lines containing either OX19 (genotypes 14, 15, 19) or OX23 (genotypes 16, 17, 18) were selected. Seeds of these lines were germinated and grown in two replicates on hydroponic medium containing no additional Zn (0 µM Zn; Zn deficiency), 2 µM Zn (normal Zn), or 25 µM Zn (excess Zn). Plants were photographed after 6 weeks and sampled for biomass analysis.

Figure 9:
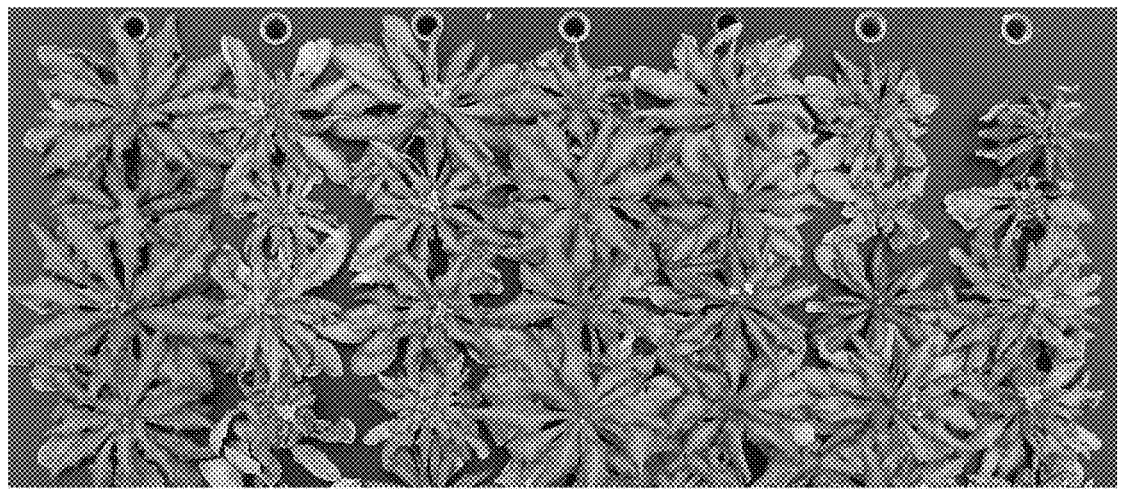
FIG. 9: Visible phenotypes of OX 19 (#19, 14, 15), OX 23 (#16, 17, 18) and untransformed *Arabidopsis* Col plants (WT), grown for 6 weeks on hydroponics medium to which no Zn has been added (0 μM Zn), creating strong zinc deficiency symptoms. Lines 19, 16 and 17 appear to have larger rosettes and darker green leaves, showing less sensitivity to zinc deficiency, when compared to WT.
Figure 10:
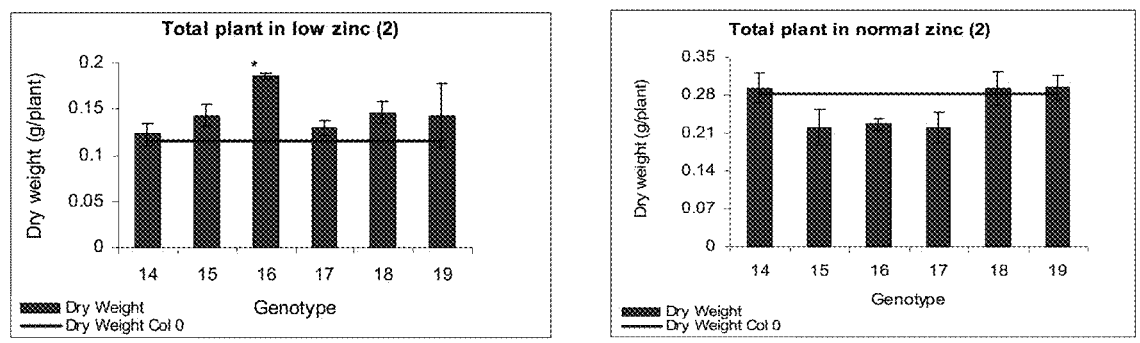
FIG. 10:: Total plant dry weight comparisons of OX 19 (#19, 14, 15), OX 23 (#16, 17, 18) and untransformed *Arabidopsis* Col plants (WT), grown for 6 weeks on hydroponics medium to which no Zn has been added (0 μM Zn)(A, left panel); or on hydroponic medium containing normal Zn (2 µM Zn) (B, right panel). Only for the low Zn treatment, line #16 was found to be significantly different from WT.
Figure 11:
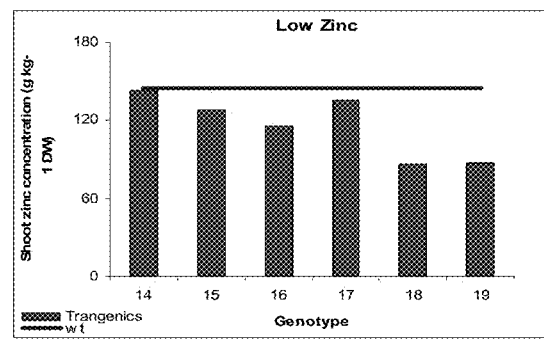
FIG. 11: Zinc concentrations of OX 19 (#19, 14, 15), OX 23 (#16, 17, 18) and untransformed *Arabidopsis* Col plants (WT), grown for 6 weeks on hydroponics medium to which no Zn has been added (0 µM Zn).

When comparing plants grown at normal Zn conditions, there was no obvious difference in visible phenotype (data not shown). However, when plants grown on Zn deficient medium were compared, lines 19 (OX 19), 16 and 17 (OX23) were generally larger and greener (FIG. 9). When examined for biomass production, indeed all lines were found to produce more biomass than WT, although at this small scale experiment, this was only found to be significant for line #16 (FIG. 10A). When plants grown at normal Zn supply were examined for biomass production, they were generally found to have less or equal biomass compared to WT (FIG. 10B), although the observed differences were not statistically significant. Zinc concentrations were determined in shoots of all lines grown at normal zinc and zinc deficiency. The shoot Zn concentrations of plants grown at normal zinc were generally not different from WT (data not shown), however, at zinc deficiency, the concentration of zinc in all lines was lower than WT (FIG. 11), with especially lines 18 and 19 showing only 60% of the Zn concentration of WT. This means that although plants are not able to acquire more Zn, due to depletion of Zn in the medium, some OX 19 and OX23 lines are able to produce more biomass with the same amount of Zn, indicating they are more Zn deficiency tolerant and more Zn efficient.

Example 3

For this experiment, a new pZIP4::bZIP19 construct was made. This contains the full Arabidopsis bZIP19 cDNA fused downstream of the promoter of the zinc deficiency responsive Arabidopsis ZIP4 gene. The rationale of the experiments is to test if overexpression of bZIP19 or bZIP23 function will enhance the tolerance to Zn deficiency, compared to wild type Arabidopsis plants. Overexpression of bZIP19 function in this experiment, in contrast with the experiment described in Example 2, is mediated by the promoter of the Zn deficiency transcriptionally responsive ZIP4 zinc transporter gene. Thus, overexpression of bZIP19 function will be predominantly in the cells and tissues in which normally the Zn deficiency response is active, albeit expected at higher levels than in WT plants.

Figure 12:
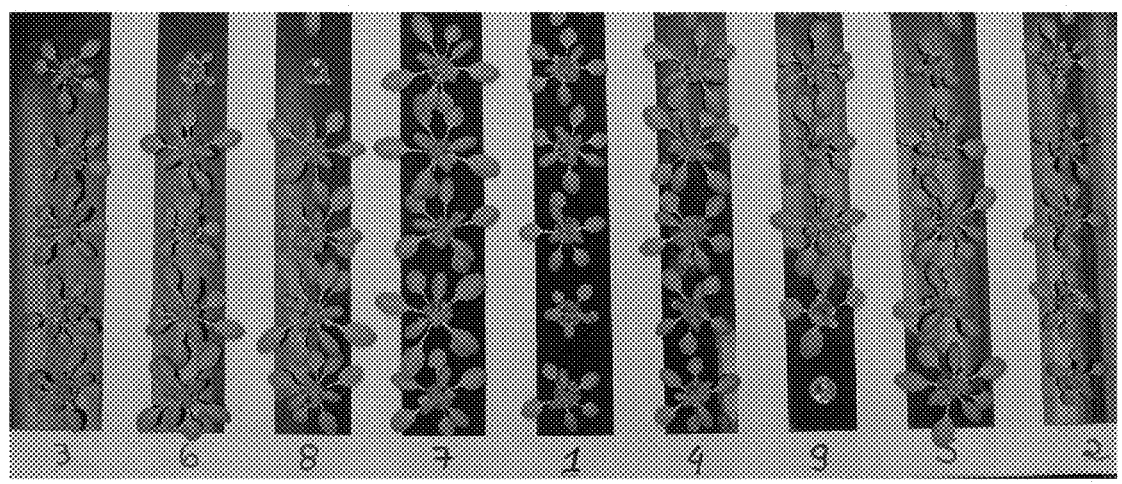
FIG. 12: Visible phenotypes of pZIP4::bZIP19 (#4, 5, 6, 7, 8, 9) and untransformed *Arabidopsis* Col plants (#1, 2, 3), grown for 3 weeks on hydroponics medium to which no Zn has been added (0 µM Zn). Plants are not yet showing Zn deficiency symptoms. Although there is some variation within lines due to plants that germinated later than the rest, in general, pZIP4::bZIP19 plants are showing larger rosette diameters than untransformed plants.
Figure 13:
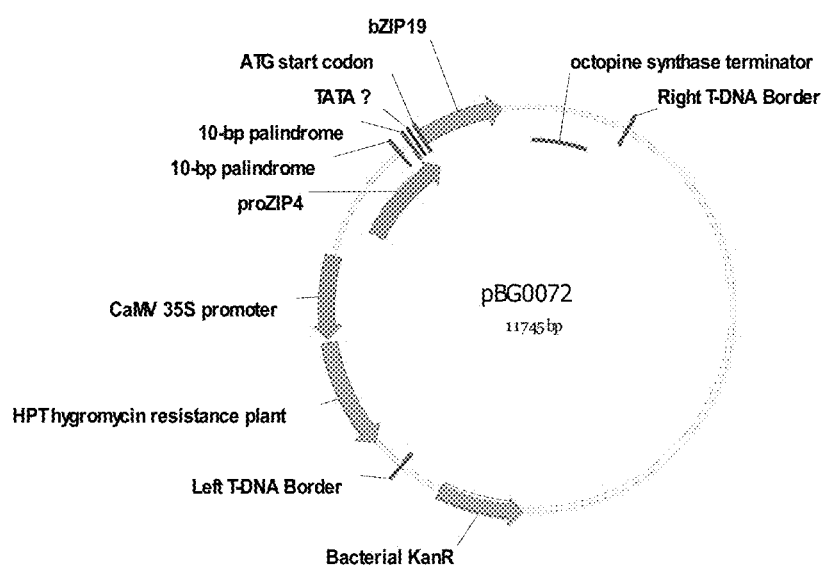
FIG. 13: Schematic drawing of the proZIP4::bZIP19 construct (pBG0072) used to generate transgenic *Arabidopsis* expressing the bZIP19 cDNA under control of the zinc deficiency responsive ZIP4 promoter.

Arabidopsis plants, accession Col, were transformed with the pZIP4::bZIP19 construct and homozygous T3 plants were obtained. In total 6 lines were selected, containing the T-DNA inserted at one locus and showing an undiminished hygromycin resistance phenotype after three successive generations as evidence of stable transformation. WT and pZIP4::bZIP19 plants were grown in two replicates on medium with normal Zn (2 µM Zn), or with no Zn added (0 µM Zn) to cause Zn deficiency. After four weeks of growth, photos were taken to determine any differences in visible phenotypes (FIG. 12). At this stage, plants are not yet showing visible Zn deficiency symptoms, but show growth retardation, compared to plant grown on normal Zn (data not shown). At this stage, it is clear that WT plants in general have smaller rosettes than pZIP4::bZIP19 transformed plants.

The invention claimed is:

1. A method to produce a modified plant, said method comprising providing said plant with a nucleic acid encoding SEQ ID NO: 1 operably linked to a promoter induced by zinc deficiency.

2. The method of claim 1, wherein said modified plant is grown under zinc deficiency conditions and exhibits increased tolerance to Zn deficiency as compared to an unmodified plant.

3. The method of claim 1, wherein said modified plant is grown under zinc deficiency conditions and has increased biomass as compared to an unmodified plant.

4. The method of claim 1, wherein said modified plant is further provided with a nucleic acid encoding bZIP23 SEQ ID NO: 2.

5. The method of claim 1, wherein said modified plant is additionally provided with one or more nucleic acids that encode a protein selected from the group consisting of heavy metal-associated (HMA), yellow stripe 1-like (YSL), zinc regulated transporter IRT-like protein (ZIP), iron-regulated transporter (IRT), zinc induced facilitator (ZIF), nicotianamine synthase (NAS), multidrug resistance protein (MRP), ferric reductase defective 3 (FRD3) and metal tolerance proteins (MTPs).

6. The method of claim 5 wherein the protein is selected from the group consisting of HMA2, HMA3, HMA4, YSL1, and YSL3.

7. The method of claim 1, wherein said promoter is the ZIP4 promoter.

* * * * *

SEQUENCE LISTING

<160> NUMBER OF SEQ ID NOS: 44

<210> SEQ ID NO 1
<211> LENGTH: 249
<212> TYPE: PRT
<213> ORGANISM: Arabidopsis thaliana

<400> SEQUENCE: 1

```
Met Asp Asp Gly Glu Leu Glu Phe Ser Asn Ser Asn Met Gly Gly Glu
1               5                   10                  15

Leu Pro Ser Cys Ser Met Asp Ser Phe Phe Asp Glu Leu Leu Arg Asp
            20                  25                  30

Ser His Ala Cys Thr His Thr His Thr Cys Asn Pro Pro Gly Pro Glu
        35                  40                  45

Asn Thr His Thr His Thr Cys Leu His Val His Thr Lys Ile Leu Pro
    50                  55                  60

Asp Lys Val Ser Thr Asp Thr Ser Glu Ser Ser Gly Lys Lys Arg
65                  70                  75                  80

Pro Leu Gly Asn Arg Glu Ala Val Arg Lys Tyr Arg Glu Lys Lys Lys
                85                  90                  95

Ala Lys Ala Ala Ser Leu Glu Asp Glu Val Met Arg Leu Lys Ala Val
            100                 105                 110

Asn Asn Gln Leu Leu Lys Arg Leu Gln Gly Gln Ala Ala Leu Glu Ala
        115                 120                 125

Glu Val Thr Arg Leu Lys Cys Leu Leu Val Asp Ile Arg Gly Arg Ile
    130                 135                 140

Asp Gly Glu Ile Gly Ala Phe Pro Tyr Gln Lys Pro Ala Val Thr Asn
145                 150                 155                 160

Val Pro Tyr Ser Tyr Met Met His Pro Cys Asn Met Gln Cys Asp Val
                165                 170                 175

Asp Asn Leu Tyr Cys Leu Gln Asn Gly Asn Asn Gly Glu Gly Ala Ser
            180                 185                 190

Met Asn Glu Gln Gly Leu Asn Gly Cys Glu Phe Asp Gln Leu Glu Cys
        195                 200                 205

Leu Ala Asn Gln Asn Leu Ala Gly Lys Glu Ile Pro Val Cys Ser Asn
    210                 215                 220

Gly Ile Gly Thr Phe Thr Val Asn Gly Ser Gly Val Asn Lys Arg Lys
225                 230                 235                 240

Gly Glu Pro Arg Ala Ala Lys Ala Val
                245
```

<210> SEQ ID NO 2
<211> LENGTH: 261
<212> TYPE: PRT
<213> ORGANISM: Arabidopsis thaliana

<400> SEQUENCE: 2

```
Met Glu Asp Gly Glu Leu Asp Phe Ser Asn Gln Glu Val Phe Ser Ser
1               5                   10                  15

Ser Glu Met Gly Glu Leu Pro Pro Ser Asn Cys Ser Met Asp Ser Phe
            20                  25                  30

Phe Asp Gly Leu Leu Met Asp Thr Asn Ala Ala Cys Thr His Thr His
        35                  40                  45

Thr Cys Asn Pro Thr Gly Pro Glu Asn Thr His Thr His Thr Cys Phe
    50                  55                  60

His Val His Thr Lys Ile Leu Pro Asp Glu Ser Asp Glu Lys Val Ser
```

```
            65                  70                  75                  80
Thr Asp Asp Thr Ala Glu Ser Cys Gly Lys Lys Gly Glu Lys Arg Pro
                    85                  90                  95
Leu Gly Asn Arg Glu Ala Val Arg Lys Tyr Arg Glu Lys Lys Lys Ala
                    100                 105                 110
Lys Ala Ala Ser Leu Glu Asp Glu Val Ala Arg Leu Arg Ala Val Asn
                    115                 120                 125
Gln Gln Leu Val Lys Arg Leu Gln Asn Gln Ala Thr Leu Glu Ala Glu
                    130                 135                 140
Val Ser Arg Leu Lys Cys Leu Leu Val Asp Leu Arg Gly Arg Ile Asp
145                 150                 155                 160
Gly Glu Ile Gly Ser Phe Pro Tyr Gln Lys Pro Met Ala Ala Asn Ile
                    165                 170                 175
Pro Ser Phe Ser His Met Met Asn Pro Cys Asn Val Gln Cys Asp Asp
                    180                 185                 190
Glu Val Tyr Cys Pro Gln Asn Val Phe Gly Val Asn Ser Gln Glu Gly
                    195                 200                 205
Ala Ser Ile Asn Asp Gln Gly Leu Ser Gly Cys Asp Phe Asp Gln Leu
                    210                 215                 220
Gln Cys Met Ala Asn Gln Asn Leu Asn Gly Asn Gly Asn Gly Ser Phe
225                 230                 235                 240
Ser Asn Val Asn Thr Ser Val Ser Asn Lys Arg Lys Gly Gly His Arg
                    245                 250                 255
Ala Ser Arg Ala Val
            260

<210> SEQ ID NO 3
<211> LENGTH: 228
<212> TYPE: PRT
<213> ORGANISM: Arabidopsis thaliana

<400> SEQUENCE: 3

Met Phe Cys Cys Cys Lys Asp Cys Arg Gly Asn Gln Arg Val Ser Asn
1               5                   10                  15
Phe Asp Ser Leu Thr Gly Val Phe Phe Gly Asp Leu Glu Phe Gly Pro
                20                  25                  30
Gln Asn Gln Arg Tyr Ile Lys Met Asn Glu Glu Glu Asp Lys Asp Gln
            35                  40                  45
Asp Arg Val Thr Arg Gly Cys Ser His Thr His Ser Cys Asn Pro Pro
        50                  55                  60
Gly Pro Glu Asp Ala Ser His Ser His Thr Cys Phe His Ala His Thr
65                  70                  75                  80
His Leu Ile Ile Ser Gln Asp Gln Gln Glu Asn Asp His Ser Asp Ser
                85                  90                  95
Ser Asn Lys Lys Arg Leu Cys Gly Asn Arg Glu Ala Val Arg Lys Tyr
                100                 105                 110
Arg Glu Lys Lys Lys Ala Arg Thr Ala Tyr Leu Glu Asp Glu Val Met
                115                 120                 125
Arg Leu Gln Ser Leu Asn Glu Gln Phe Leu Arg Lys Leu Gln Ser Gln
            130                 135                 140
Glu Met Val Glu Thr Glu Leu Ile Arg Leu Arg Ala Leu Leu Val Glu
145                 150                 155                 160
Met Gln Gly Lys Ile Glu Val Glu Leu Cys Ser Phe Ser Phe Gln Lys
                165                 170                 175
```

Gln Cys Asn Gly Ser Gly Phe Val Phe Lys Glu Asp Gly Cys Asn Leu
              180                 185                 190

Ala Thr Ser Asn Met Met Cys Glu Ala Ala Arg Val Glu Cys Glu Glu
          195                 200                 205

Gly Gln Thr Leu His Asp Pro Ile Gln Ser Phe Val Pro Gln Pro Pro
      210                 215                 220

Pro Phe Ser Arg
225

<210> SEQ ID NO 4
<211> LENGTH: 11745
<212> TYPE: DNA
<213> ORGANISM: Artificial
<220> FEATURE:
<223> OTHER INFORMATION: construct pBG0072

<400> SEQUENCE: 4
ctagagtcct gctttaatga gatatgcgag acgcctatga tcgcatgata tttgctttca    60
attctgttgt gcacgttgta aaaaacctga gcatgtgtag ctcagatcct taccgccggt   120
ttcggttcat tctaatgaat atatcacccg ttactatcgt attttttatga ataatattct   180 ccgttcaatt tactgattgt accctactac ttatatgtac aatattaaaa tgaaaacaat   240
atattgtgct gaataggttt atagcgacat ctatgataga gcgccacaat aacaaacaat   300
tgcgttttat tattacaaat ccaattttaa aaaagcggc agaaccggtc aaacctaaaa    360
gactgattac ataaatctta ttcaaatttc aaagtgccc caggggctag tatctacgac    420
acaccgagcg gcgaactaat aacgctcact gaagggaact ccggttcccg ccggcgcgca   480
tgggtgagat tccttgaagt tgagtattgg ccgtccgctc tacgaaagtt acgggcacca   540
ttcagcgaca acatgtcgag gctcagcagg acctgcaggc atgcaaaaaa aaaaactagt   600
gatgcatatt ctatagtgtc acctaaatct gcggccgctg accaagtcag ctagcttggc   660
actggccgtc gttttacaac gtcgtgactg gaaaaccct ggcgttaccc aacttaatcg    720
ccttgcagca catccccctt tcgccagctg gcgtaatagc gaagaggccc gcaccgatcg   780
cccttcccaa cagttgcgca gcctgaatgg cgaatgctag agcagcttga gcttggatca   840
gattgtcgtt tcccgccttc agtttaaact atcagtgttt gacaggatat attggcgggt   900
aaacctaaga gaaagagcg tttattagaa taacggatat ttaaaagggc gtgaaaaggt   960
ttatccgttc gtccatttgt atgtgcatgc caaccacagg gttcccctcg ggatcaaagt  1020
actttgatcc aaccctccg ctgctatagt gcagtcggct tctgacgttc agtgcagccg   1080
tcttctgaaa acgacatgtc gcacaagtcc taagttacgc gacaggctgc cgccctgccc  1140
ttttcctggc gttttcttgt cgcgtgtttt agtcgcataa agtagaatac ttgcgactag  1200
aaccggagac attacgccat gaacaagagc gccgccgctg gcctgctggg ctatgcccgc  1260
gtcagcaccg acgaccagga cttgaccaac aacgggccg aactcacgc ggccggctgc    1320 accaagctgt tttccgagaa gatcaccggc accaggcgcg accgcccgga gctggccagg  1380
atgcttgacc acctacgccc tggcgacgtt gtgacagtga ccaggctaga ccgcctggcc  1440
cgcagcaccc gcgacctact ggacattgcc gagcgcatcc aggaggccgg cgcgggcctg  1500
cgtagcctgg cagagccgtg ggccgacacc accacgccgg ccggccgcat ggtgttgacc  1560
gtgttcgccg gcattgccga gttcgagcgt tccctaatca tcgaccgcac ccggagcggg  1620
cgcgaggccc caaggcccg aggcgtgaag tttggccccc gccctaccct caccccggca  1680
cagatcgcgc acgcccgcga gctgatcgac caggaaggcc gcaccgtgaa agaggcggct  1740

```
gcactgcttg gcgtgcatcg ctcgaccctg taccgcgcac ttgagcgcag cgaggaagtg    1800
acgcccaccg aggccaggcg gcgcggtgcc ttccgtgagg acgcattgac cgaggccgac    1860
gccctggcgg ccgccgagaa tgaacgccaa gaggaacaag catgaaaccg caccaggacg    1920
gccaggacga accgtttttc attaccgaag agatcgaggc ggagatgatc gcggccgggt    1980
acgtgttcga gccgcccgcg cacgtctcaa ccgtgcggct gcatgaaatc ctggccggtt    2040
tgtctgatgc caagctggcg gcctggccgg ccagcttggc cgctgaagaa accgagcgcc    2100
gccgtctaaa aaggtgatgt gtatttgagt aaaacagctt gcgtcatgcg gtcgctgcgt    2160
atatgatgcg atgagtaaat aaacaaatac gcaaggggaa cgcatgaagg ttatcgctgt    2220
acttaaccag aaaggcgggt caggcaagac gaccatcgca acccatctag cccgcgccct    2280
gcaactcgcc ggggccgatg ttctgttagt cgattccgat ccccagggca gtgcccgcga    2340
ttgggcggcc gtgcgggaag atcaaccgct aaccgttgtc ggcatcgacc gcccgacgat    2400
tgaccgcgac gtgaaggcca tcggccggcg cgacttcgta gtgatcgacg gagcgcccca    2460
ggcggcggac ttggctgtgt ccgcgatcaa ggcagccgac ttcgtgctga ttccggtgca    2520
gccaagccct tacgacatat gggccaccgc cgacctggtg gagctggtta agcagcgcat    2580
tgaggtcacg gatggaaggc tacaagcggc ctttgtcgtg tcgcgggcga tcaaaggcac    2640
gcgcatcggc ggtgaggttg ccgaggcgct ggccgggtac gagctgccca ttcttgagtc    2700
ccgtatcacg cagcgcgtga gctacccagg cactgccgcc gccggcacaa ccgttcttga    2760
atcagaaccc gagggcgacg ctgcccgcga ggtccaggcg ctggccgctg aaattaaatc    2820
aaaactcatt tgagttaatg aggtaaagag aaaatgagca aaagcacaaa cacgctaagt    2880 gccgccgtc cgagcgcacg cagcagcaag gctgcaacgt tggccagcct ggcagacacg    2940
ccagccatga agcgggtcaa cttcagttg ccggcggagg atcacaccaa gctgaagatg    3000
tacgcggtac gccaaggcaa gaccattacc gagctgctat ctgaatacat cgcgcagcta    3060
ccagagtaaa tgagcaaatg aataaatgag tagatgaatt ttagcggcta aaggaggcgg    3120
catgaaaaat caagaacaac caggcaccga cgccgtggaa tgccccatgt gtggaggaac    3180
gggcggttgg ccaggcgtaa gcggctgggt tgtctgccgg ccctgcaatg gcactggaac    3240
ccccaagccc gaggaatcgg cgtgacggtc gcaaaccatc cggcccggta caatcggcg    3300 cggcgctggg tgatgacctg gtggagaagt tgaaggccgc gcaggccgcc cagcggcaac    3360
gcatcgaggc agaagcacgc cccggtgaat cgtggcaagc ggccgctgat cgaatccgca    3420
aagaatcccg gcaaccgccg gcagccggtg cgccgtcgat taggaagccg cccaagggcg    3480
acgagcaacc agattttttc gttccgatgc tctatgacgt gggcacccgc gatagtcgca    3540
gcatcatgga cgtggccgtt ttccgtctgt cgaagcgtga ccgacgagct ggcgaggtga    3600
tccgctacga gcttccagac gggcacgtag aggtttccgc agggccggcc ggcatggcca    3660
gtgtgtggga ttacgacctg gtactgatgg cggtttccca tctaaccgaa tccatgaacc    3720
gataccggga agggaaggga gacaagcccg gccgcgtgtt ccgtccacac gttgcggacg    3780
tactcaagtt ctgccggcga gccgatggcg gaaagcagaa agacgacctg gtagaaacct    3840
gcattcggtt aaacaccacg cacgttgcca tgcagcgtac gaagaaggcc aagaacggcc    3900
gcctggtgac ggtatccgag ggtgaagcct tgattagccg ctacaagatc gtaaagagcg    3960
aaaccgggcg gccggagtac atcgagatcg agctagctga ttggatgtac cgcgagatca    4020
cagaaggcaa gaacccggac gtgctgacgg ttcaccccga ttactttttg atcgatcccg    4080
```

```
gcatcggccg tttctctac cgcctggcac gccgcgccgc aggcaaggca gaagccagat    4140
ggttgttcaa gacgatctac gaacgcagtg cagcgccgg agagttcaag aagttctgtt    4200
tcaccgtgcg caagctgatc gggtcaaatg acctgccgga gtacgatttg aaggaggagg    4260
cggggcaggc tggcccgatc ctagtcatgc gctaccgcaa cctgatcgag ggcgaagcat    4320
ccgccggttc ctaatgtacg gagcagatgc tagggcaaat tgccctagca ggggaaaaag    4380
gtcgaaaagg tctctttcct gtggatagca cgtacattgg gaacccaaag ccgtacattg    4440
ggaaccggaa cccgtacatt gggaacccaa agccgtacat tgggaaccgg tcacacatgt    4500
aagtgactga tataaaagag aaaaaaggcg attttccgc ctaaaactct ttaaaactta    4560
ttaaaactct taaacccgc ctggcctgtg cataactgtc tggccagcgc acagccgaag    4620
agctgcaaaa agcgcctacc cttcggtcgc tgcgctccct acgccccgcc gcttcgcgtc    4680
ggcctatcgc ggccgctggc cgctcaaaaa tggctggcct acggcaggc aatctaccag    4740
ggcgcggaca agccgcgccg tcgccactcg accgccggcg cccacatcaa ggcaccctgc    4800
ctcgcgcgtt tcggtgatga cggtgaaaac ctctgacaca tgcagctccc ggagacggtc    4860
acagcttgtc tgtaagcgga tgccgggagc agacaagccc gtcagggcgc gtcagcgggt    4920
gttggcgggt gtcggggcgc agccatgacc cagtcacgta gcgatagcgg agtgtatact    4980
ggcttaacta tgcggcatca gagcagattg tactgagagt gcaccatatg cggtgtgaaa    5040
taccgcacag atgcgtaagg agaaaatacc gcatcaggcg ctcttccgct tcctcgctca    5100
ctgactcgct gcgctcggtc gttcggctgc ggcgagcggt atcagctcac tcaaaggcgg    5160
taatacggtt atccacagaa tcaggggata acgcaggaaa gaacatgtga gcaaaaggcc    5220
agcaaaaggc caggaaccgt aaaaaggccg cgttgctggc gtttttccat aggctccgcc    5280
cccctgacga gcatcacaaa aatcgacgct caagtcagag gtggcgaaac ccgacaggac    5340
tataagata ccaggcgttt ccccctggaa gctccctcgt gcgctctcct gttccgaccc    5400
tgccgcttac cggatacctg tccgcctttc tcccttcggg aagcgtggcg ctttctcata    5460
gctcacgctg taggtatctc agttcggtgt aggtcgttcg ctccaagctg ggctgtgtgc    5520
acgaacccc cgttcagccc gaccgctgcg ccttatccgg taactatcgt cttgagtcca    5580
acccggtaag acacgactta tcgccactgg cagcagccac tggtaacagg attagcagag    5640
cgaggtatgt aggcggtgct acagagttct tgaagtggtg gcctaactac ggctacacta    5700
gaaggacagt atttggtatc tgcgctctgc tgaagccagt taccttcgga aaaagagttg    5760
gtagctcttg atccggcaaa caaaccaccg ctggtagcgg tggtttttt gtttgcaagc    5820
agcagattac gcgcagaaaa aaaggatctc aagaagatcc tttgatcttt tctacggggt    5880
ctgacgctca gtggaacgaa aactcacgtt aagggatttt ggtcatgcat tctaggtact    5940
aaaacaattc atccagtaaa atataatatt ttatttctc ccaatcaggc ttgatcccca    6000
gtaagtcaaa aaatagctcg acatactgtt cttccccgat atcctccctg atcgaccgga    6060
cgcagaaggc aatgtcatac cacttgtccg ccctgccgct tctcccaaga tcaataaagc    6120
cacttacttt gccatctttc acaaagatgt tgctgtctcc caggtcgccg tgggaaaaga    6180
caagttcctc ttcgggcttt tccgtcttta aaaaatcata cagctcgcgc ggatctttaa    6240
atggagtgtc ttcttcccag ttttcgcaat ccacatcggc cagatcgtta ttcagtaagt    6300
aatccaattc ggctaagcgg ctgtctaagc tattcgtata gggacaatcc gatatgtcga    6360
tggagtgaaa gagcctgatg cactccgcat acagctcgat aatctttca gggctttgtt    6420
catcttcata ctcttccgag caaaggacgc catcggcctc actcatgagc agattgctcc    6480
```

```
agccatcatg ccgttcaaag tgcaggacct ttggaacagg cagctttcct tccagccata   6540
gcatcatgtc cttttcccgt tccacatcat aggtggtccc tttataccgg ctgtccgtca   6600
ttttaaaata taggttttca ttttctccca ccagcttata taccttagca ggagacattc   6660
cttccgtatc ttttacgcag cggtattttt cgatcagttt tttcaattcc ggtgatattc   6720
tcattttagc catttattat ttccttcctc ttttctacag tatttaaaga tacccccaaga  6780
agctaattat aacaagacga actccaattc actgttcctt gcattctaaa accttaaata   6840
ccagaaaaca gcttttccaa agttgttttc aaagttggcg tataacatag tatcgacgga   6900
gccgattttg aaaccgcggt gatcacaggc agcaacgctc tgtcatcgtt acaatcaaca   6960
tgctaccctc cgcgagatca tccgtgtttc aaacccggca gcttagttgc cgttcttccg   7020
aatagcatcg gtaacatgag caaagtctgc cgccttacaa cggctctccc gctgacgccg   7080
tcccggactg atgggctgcc tgtatcgagt ggtgattttg tgccgagctg ccggtcgggg   7140
agctgttggc tggctggtgg caggatatat tgtggtgtaa acaaattgac gcttagacaa   7200
cttaataaca cattgcggac gttttaatg tactgaatta cgccgaatt aattcggggg     7260
atctggattt tagtactgga ttttggtttt aggaattaga aattttattg atagaagtat    7320
tttacaaata caaatacata ctaagggttt cttatatgct caacacatga gcgaaaccct   7380
ataggaaccc taattccctt atctgggaac tactcacaca ttattatgga gaaactcgag   7440
cttgtcgatc gacagatccg gtcggcatct actctatttc tttgccctcg gacgagtgct   7500
gggggcgtcg ttccactat cggcgagtac ttctacacag ccatcggtcc agacggccgc    7560
gcttctgcgg gcgatttgtg tacgcccgac agtcccggct ccggatcgga cgattgcgtc   7620
gcatcgaccc tgcgcccaag ctgcatcatc gaaattgccg tcaaccaagc tctgatagag   7680
ttggtcaaga ccaatgcgga gcatatacgc ccggagtcgt ggcgatcctg caagctccgg   7740
atgcctccgc tcgaagtagc gcgtctgctg ctccatacaa gccaaccacg gcctccagaa   7800
gaagatgttg gcgacctcgt attgggaatc cccgaacatc gcctcgctcc agtcaatgac   7860
cgctgttatg cggccattgt ccgtcaggac attgttggag ccgaaatccg cgtgcacgag   7920
gtgccggact tcggggcagt cctcggccca aagcatcagc tcatcgagag cctgcgcgac   7980
ggacgcactg acggtgtcgt ccatcacagt ttgccagtga tacacatggg gatcagcaat   8040
cgcgcatatg aaatcacgcc atgtagtgta ttgaccgatt ccttgcggtc cgaatgggcc   8100
gaacccgctc gtctggctaa gatcggccgc agcgatcgca tccatagcct ccgcgaccgg   8160
ttgtagaaca gcgggcagtt cggtttcagg caggtcttgc aacgtgacac cctgtgcacg   8220
gcgggagatg caataggtca ggctctcgct aaactcccca atgtcaagca cttccggaat   8280
cgggagcgcg gccgatgcaa agtgccgata aacataacga tctttgtaga aaccatcggc   8340
gcagctattt acccgcagga catatccacg ccctcctaca tcgaagctga agcacgaga    8400
ttcttcgccc tccgagagct gcatcaggtc ggagacgctg tcgaactttt cgatcagaaa   8460
cttctcgaca gacgtcgcgg tgagttcagg ctttttcata tctcattgcc ccccggatc    8520
tgcgaaagct cgagagagat agatttgtag agagagactg gtgatttcag cgtgtcctct   8580
ccaaatgaaa tgaacttcct tatatagagg aaggtcttgc gaaggatagt gggattgtgc   8640
gtcatccctt acgtcagtgg agatatcaca tcaatccact tgctttgaag acgtggttgg   8700
aacgtcttct ttttccacga tgctcctcgt gggtgggggt ccatctttgg gaccactgtc   8760
ggcagaggca tcttgaacga tagcctttcc tttatcgcaa tgatggcatt tgtaggtgcc   8820
```

```
accttcctttt tctactgtcc ttttgatgaa gtgacagata gctgggcaat ggaatccgag    8880
gaggtttccc gatattaccc tttgttgaaa agtctcaata gcccttttggt cttctgagac    8940 tgtatctttg atattcttgg agtagacgag agtgtcgtgc tccaccatgt tatcacatca    9000
atccacttgc tttgaagacg tggttggaac gtcttctttt tccacgatgc tcctcgtggg    9060
tgggggtcca tctttgggac cactgtcggc agaggcatct tgaacgatag cctttccttt    9120
atcgcaatga tggcatttgt aggtgccacc ttccttttct actgtccttt tgatgaagtg    9180
acagatagct gggcaatgga atccgaggag gtttcccgat attaccctt gttgaaaagt    9240 ctcaatagcc ctttggtctt ctgagactgt atctttgata ttcttggagt agacgagagt    9300
gtcgtgctcc accatgttgg caagctgctc tagccaatac gcaaaccgcc tctcccgcg    9360 cgttggccga ttcattaatg cagctggcac gacaggtttc ccgactggaa agcgggcagt    9420
gagcgcaacg caattaatgt gagttagctc actcattagg caccccaggc tttacacttt    9480
atgcttccgg ctcgtatgtt gtgtggaatt gtgagcggat aacaatttca cacaggaaac    9540
agctatgacc atgattacga atttggccaa gtcggcctct aatacgactc actataggga    9600
gctcggtacc cggggatcct ctagagtcga cctgcaggca tgcaagcttt ggaaagtgaa    9660
gtggattgtt ccaacacttt ggtacatcct ttcttatgca atgttggtac tgatttgcct    9720
cttttggcct ccatcggaaa aaccaatgag gtatggtatc aatctttctg tacttgccct    9780
ttatcaatcg ggtgcttatg tggcctgttt taagttccac actaagatct tgtctgtttt    9840
gtactaacat gtttgaactt tgtatatctg atcttctctg ctgctagtta cacattttc    9900 tgatgtatat atactggttt gaaattgcag gtacctatac gtagctgaca tggaggaaga    9960
gactgaagaa gaagatgatc tctccactgc agaaaccggt atgaacgcaa caaaggctga   10020
atacgagagg agtgaaagga agaccctgct ggaagcattc atcctattgc ttgggaatat   10080
accaggggag aagtgaaact ccccatctta caaagttacc gtccttttag cttaagctgc   10140
ctacttctca tccttttca gcttaagcta ctcctaatca tccttttaaa cctacggctt   10200
taagtttttt tttaactcat ataatcttct gcagtagact tgacttaatc ggattttctg   10260
tttcatgaac ttgttggtag tgtggaacaa atgggaaaat gaatatttt ggaacaaatt   10320 gattttctgt ttcatattaa gttaaatcat tctgtttcca ctgaaataaa ttgttttcca   10380
aaaatcactc cgtttattat gtctttgttt ttaagaaata aaagtgagaa acagaataa    10440 cgcgaaaatg tcgacatatt tggctaagta tagacaagat tgggaagctc tgtttagtta   10500
tgcgtcagtc tctcatcagt gttcaactgc cacggagcga accgattcct aattgcaacg   10560
tcccgagtcc atagaatgtc gacactcttt cactctttct ccaagttgcc tcctttgagt   10620
cctttctcat attttataga ctcactttct gtttcttgat cccgaggaag aagaagaata   10680
aactcttgtt cccatggaag acggtgagct tgatttctcc aatcaggaag tgttttcgag   10740
ttcggagatg ggtgaattac cacctagcaa ttgttcgatg gatagtttct ttgatgggct   10800
tttaatggat actaatgctg cttgtaccca cactcacacc tgtaacccca ctggaccaga   10860
gaacactcat actcacacgt gcttccatgt ccacaccaag attctcccgg atgagagcga   10920
tgaaaaagtt tctactgatg atacagctga gtcttgtggg aagaagggtg aaaagagacc   10980
tttgggaaac cgggaagcgg ttagaaagta tagagagaag aagaaggcta agctgcttc    11040 tttggaggat gaggttgcaa ggcttagggc ggtgaatcag cagctggtga agaggttgca   11100
aaatcaggct accttggaag ctgaggtttc gaggcttaag tgtttgcttg tggatttgag   11160
aggaagaata gatggagaga ttggatcttt tccttatcag aaacctatgg ctgcaaatat   11220
```

```
tccttctttc tcgcacatga tgaatccttg taatgtacaa tgtgatgatg aagtttattg   11280
ccctcagaat gtgtttggag tgaatagcca agaaggtgcc tcgatcaatg accaagggtt   11340
aagtggttgt gattttgatc agctacaatg catggctaat cagaacttaa atggaaatgg   11400
aaacggatca ttcagcaacg tcaatacatc tgtctcgaat aagagaaaag gtgggcatcg   11460
tgcatcaaga gcagtttgaa gcatcatcaa gcttgtacta tctatttcca ccagcataga   11520
tattgtattc caaataagtt gtagagttca gctgcaggat cagcttcgct caggttcctt   11580
tgtatcctca tttttgtttt tgtttctg actctctttc ccttccattg tatttccttg   11640
ttgagcttga caaactagaa ggatgatata ttgttaatac aacaaactca aatgttctgt   11700
gtgttcttgc catttgtttt catacttgag ctgcttcttc ttaaa                   11745
```

<210> SEQ ID NO 5
<211> LENGTH: 49
<212> TYPE: DNA
<213> ORGANISM: Artificial
<220> FEATURE:
<223> OTHER INFORMATION: primer

<400> SEQUENCE: 5
ggggacaagt ttgtacaaaa aagcaggctt aactcttgtt cccatgatc              49

<210> SEQ ID NO 6
<211> LENGTH: 48
<212> TYPE: DNA
<213> ORGANISM: Artificial
<220> FEATURE:
<223> OTHER INFORMATION: primer

<400> SEQUENCE: 6
ggggaccact ttgtacaaga aagctgggta tattatttga ttctacag               48

<210> SEQ ID NO 7
<211> LENGTH: 10
<212> TYPE: DNA
<213> ORGANISM: Artificial
<220> FEATURE:
<223> OTHER INFORMATION: bait motif reporter vector G

<400> SEQUENCE: 7 atgtcgacay                                                         10

<210> SEQ ID NO 8
<211> LENGTH: 28
<212> TYPE: DNA
<213> ORGANISM: Artificial
<220> FEATURE:
<223> OTHER INFORMATION: primer

<400> SEQUENCE: 8
gaattcaagc tttggaaagt gaagtgga                                     28

<210> SEQ ID NO 9
<211> LENGTH: 22
<212> TYPE: DNA
<213> ORGANISM: Artificial
<220> FEATURE:
<223> OTHER INFORMATION: primer

<400> SEQUENCE: 9
gagctccaat ttcaaaccag ta                                           22

<210> SEQ ID NO 10
<211> LENGTH: 29
<212> TYPE: DNA
<213> ORGANISM: Artificial
<220> FEATURE:
<223> OTHER INFORMATION: primer

<400> SEQUENCE: 10
gaattctgta tatctgatct tctctgctg                              29

<210> SEQ ID NO 11
<211> LENGTH: 26
<212> TYPE: DNA
<213> ORGANISM: Artificial
<220> FEATURE:
<223> OTHER INFORMATION: primer

<400> SEQUENCE: 11
gagctcaagc taaaaggacg gtaact                                 26

<210> SEQ ID NO 12
<211> LENGTH: 23
<212> TYPE: DNA
<213> ORGANISM: Artificial
<220> FEATURE:
<223> OTHER INFORMATION: primer

<400> SEQUENCE: 12
gaattcttca tcctattgct tgg                                    23

<210> SEQ ID NO 13
<211> LENGTH: 25
<212> TYPE: DNA
<213> ORGANISM: Artificial
<220> FEATURE:
<223> OTHER INFORMATION: primer

<400> SEQUENCE: 13
gagctcattt tcccatttgt tccac                                  25

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
gaattctctg cagtagactt gac                                    23

<210> SEQ ID NO 15
<211> LENGTH: 21
<212> TYPE: DNA
<213> ORGANISM: Artificial
<220> FEATURE:
<223> OTHER INFORMATION: primer

<400> SEQUENCE: 15
gagctcccca atcttgtcta t                                      21

<210> SEQ ID NO 16
<211> LENGTH: 30
<212> TYPE: DNA
<213> ORGANISM: Artificial
<220> FEATURE:
<223> OTHER INFORMATION: primer -continued

```
<400> SEQUENCE: 16
atcggaattc gtgagaaaac agaataacgc                                          30

<210> SEQ ID NO 17
<211> LENGTH: 26
<212> TYPE: DNA
<213> ORGANISM: Artificial
<220> FEATURE:
<223> OTHER INFORMATION: primer

<400> SEQUENCE: 17
gagctcccat gggaacaaga gtttat                                              26

<210> SEQ ID NO 18
<211> LENGTH: 30
<212> TYPE: DNA
<213> ORGANISM: Artificial
<220> FEATURE:
<223> OTHER INFORMATION: primer

<400> SEQUENCE: 18
atcggaattc gtgagaaaac agaataacgc                                          30

<210> SEQ ID NO 19
<211> LENGTH: 30
<212> TYPE: DNA
<213> ORGANISM: Artificial
<220> FEATURE:
<223> OTHER INFORMATION: primer

<400> SEQUENCE: 19
cgtagagctc tggagaaaga gtgaaagagt                                          30

<210> SEQ ID NO 20
<211> LENGTH: 40
<212> TYPE: DNA
<213> ORGANISM: Artificial
<220> FEATURE:
<223> OTHER INFORMATION: primer

<400> SEQUENCE: 20
aattcatgtc gacatatgtc gacatatgtc gacacgagct                               40

<210> SEQ ID NO 21
<211> LENGTH: 32
<212> TYPE: DNA
<213> ORGANISM: Artificial
<220> FEATURE:
<223> OTHER INFORMATION: primer

<400> SEQUENCE: 21
cgtgtcgaca tatgtcgaca tatgtcgaca tg                                       32

<210> SEQ ID NO 22
<211> LENGTH: 22
<212> TYPE: DNA
<213> ORGANISM: Artificial
<220> FEATURE:
<223> OTHER INFORMATION: primer

<400> SEQUENCE: 22
gatcttcgtc gatgttcttt gg                                                  22

<210> SEQ ID NO 23
```

```
<211> LENGTH: 25
<212> TYPE: DNA
<213> ORGANISM: Artificial
<220> FEATURE:
<223> OTHER INFORMATION: primer

<400> SEQUENCE: 23
tgagaggtat ggctacacca gcagc                                              25

<210> SEQ ID NO 24
<211> LENGTH: 20
<212> TYPE: DNA
<213> ORGANISM: Artificial
<220> FEATURE:
<223> OTHER INFORMATION: primer

<400> SEQUENCE: 24
ggacacacac atggttcgac                                                    20

<210> SEQ ID NO 25
<211> LENGTH: 20
<212> TYPE: DNA
<213> ORGANISM: Artificial
<220> FEATURE:
<223> OTHER INFORMATION: primer

<400> SEQUENCE: 25
gatagtgcag ccatgagtgg                                                    20

<210> SEQ ID NO 26
<211> LENGTH: 25
<212> TYPE: DNA
<213> ORGANISM: Artificial
<220> FEATURE:
<223> OTHER INFORMATION: primer

<400> SEQUENCE: 26
cagaaacatg tttcttcttc gtcac                                              25

<210> SEQ ID NO 27
<211> LENGTH: 20
<212> TYPE: DNA
<213> ORGANISM: Artificial
<220> FEATURE:
<223> OTHER INFORMATION: primer

<400> SEQUENCE: 27
cgcaataaat ccggtgaacg                                                    20

<210> SEQ ID NO 28
<211> LENGTH: 20
<212> TYPE: DNA
<213> ORGANISM: Artificial
<220> FEATURE:
<223> OTHER INFORMATION: primer

<400> SEQUENCE: 28
cgggattgtt ggcgtggaat                                                    20

<210> SEQ ID NO 29
<211> LENGTH: 20
<212> TYPE: DNA
<213> ORGANISM: Artificial
<220> FEATURE:
<223> OTHER INFORMATION: primer

<400> SEQUENCE: 29
```
ccaagaccct cgaagcattg                                               20

<210> SEQ ID NO 30
<211> LENGTH: 25
<212> TYPE: DNA
<213> ORGANISM: Artificial
<220> FEATURE:
<223> OTHER INFORMATION: primer

<400> SEQUENCE: 30
caataatcat aggaatatcg cttgg                                         25

<210> SEQ ID NO 31
<211> LENGTH: 20
<212> TYPE: DNA
<213> ORGANISM: Artificial
<220> FEATURE:
<223> OTHER INFORMATION: primer

<400> SEQUENCE: 31
agaaagccat catggcagat                                               20

<210> SEQ ID NO 32
<211> LENGTH: 22
<212> TYPE: DNA
<213> ORGANISM: Artificial
<220> FEATURE:
<223> OTHER INFORMATION: primer

<400> SEQUENCE: 32
caatgttgat tgaatccttt gc                                            22

<210> SEQ ID NO 33
<211> LENGTH: 20
<212> TYPE: DNA
<213> ORGANISM: Artificial
<220> FEATURE:
<223> OTHER INFORMATION: primer

<400> SEQUENCE: 33
ccatgagaat gtccttgtga                                               20

<210> SEQ ID NO 34
<211> LENGTH: 20
<212> TYPE: DNA
<213> ORGANISM: Artificial
<220> FEATURE:
<223> OTHER INFORMATION: primer

<400> SEQUENCE: 34
atatgttggc gggtggcacg                                               20

<210> SEQ ID NO 35
<211> LENGTH: 20
<212> TYPE: DNA
<213> ORGANISM: Artificial
<220> FEATURE:
<223> OTHER INFORMATION: primer

<400> SEQUENCE: 35
gcttccctct cttgcttccg                                               20

<210> SEQ ID NO 36
<211> LENGTH: 20
<212> TYPE: DNA

<213> ORGANISM: Artificial
<220> FEATURE:
<223> OTHER INFORMATION: primer

<400> SEQUENCE: 36
taataacaac cacgtcggag                                                      20

<210> SEQ ID NO 37
<211> LENGTH: 20
<212> TYPE: DNA
<213> ORGANISM: Artificial
<220> FEATURE:
<223> OTHER INFORMATION: primer

<400> SEQUENCE: 37
agcaaagctg tgtctccaaa                                                      20

<210> SEQ ID NO 38
<211> LENGTH: 22
<212> TYPE: DNA
<213> ORGANISM: Artificial
<220> FEATURE:
<223> OTHER INFORMATION: primer

<400> SEQUENCE: 38
ttctcccgga tgagagcgat ga                                                   22

<210> SEQ ID NO 39
<211> LENGTH: 22
<212> TYPE: DNA
<213> ORGANISM: Artificial
<220> FEATURE:
<223> OTHER INFORMATION: primer

<400> SEQUENCE: 39
gctgattcac cgccctaagc ct                                                   22

<210> SEQ ID NO 40
<211> LENGTH: 20
<212> TYPE: DNA
<213> ORGANISM: Artificial
<220> FEATURE:
<223> OTHER INFORMATION: primer

<400> SEQUENCE: 40
taatcagctg ttgaagaggt                                                      20

<210> SEQ ID NO 41
<211> LENGTH: 20
<212> TYPE: DNA
<213> ORGANISM: Artificial
<220> FEATURE:
<223> OTHER INFORMATION: primer

<400> SEQUENCE: 41
tcatgtatga gtaaggcacg                                                      20

<210> SEQ ID NO 42
<211> LENGTH: 20
<212> TYPE: DNA
<213> ORGANISM: Artificial
<220> FEATURE:
<223> OTHER INFORMATION: primer

<400> SEQUENCE: 42
tctcaggatc agcaagagaa                                                      20

```
<210> SEQ ID NO 43
<211> LENGTH: 21
<212> TYPE: DNA
<213> ORGANISM: Artificial
<220> FEATURE:
<223> OTHER INFORMATION: primer

<400> SEQUENCE: 43
tcagtttcca ccatttcttg g                                              21

<210> SEQ ID NO 44
<211> LENGTH: 10
<212> TYPE: DNA
<213> ORGANISM: Artificial
<220> FEATURE:
<223> OTHER INFORMATION: synthetically constructed zinc deficiency
      response element

<400> SEQUENCE: 44 rtgtcgacay                                                           10
```